US008107700B2

(12) United States Patent  (10) Patent No.: US 8,107,700 B2
Daw et al.  (45) Date of Patent: Jan. 31, 2012

(54) SYSTEM AND METHOD FOR EFFICIENT WORKFLOW IN READING MEDICAL IMAGE DATA

(75) Inventors: Shawni L. Daw, Redmond, WA (US); Brian W. Epps, Bainbridge Island, WA (US)

(73) Assignee: Merge CAD Inc., Bellevue, WA (US)

( * ) Notice: Subject to any disclaimer, the term of this patent is extended or adjusted under 35 U.S.C. 154(b) by 688 days.

(21) Appl. No.: 12/275,423

(22) Filed: Nov. 21, 2008

(65) Prior Publication Data

US 2009/0129644 A1 May 21, 2009

Related U.S. Application Data

(60) Provisional application No. 60/989,778, filed on Nov. 21, 2007.

(51) Int. Cl.
*G06K 9/00* (2006.01)
(52) U.S. Cl. ........................................ 382/128; 382/130
(58) Field of Classification Search ........................ None
See application file for complete search history.

(56) References Cited

U.S. PATENT DOCUMENTS 6,819,785 B1 * 11/2004 Vining et al. ................. 382/128
7,590,932 B2 * 9/2009 Britton et al. ................. 715/222

* cited by examiner

*Primary Examiner* — Minh N Tang
(74) *Attorney, Agent, or Firm* — Michael Best & Friedrich LLP

(57) ABSTRACT

A system provides methods to significantly improve the efficiency of reading medical image data. The workflow panel provides a grouping of tasks for reviewing and comparing medical images. Tablets are created for each task, consolidating the tools and associated hanging protocols to efficiently perform the actions for that task. The 3D navigation point keeps the current spatial focus point within the field of view as the user transitions between series, orientations, hanging protocols, and zoom levels. The spatial zoom method provides consistent zooming of series with varying fields of view and spatial resolution. Having the ability to overlay the parametric map on any series, regardless of its orientation or field of view, allows the user to correlate the parametric map with features on the non-temporal series. Integrating all of these methods with the workflow panel allows users to quickly step through the tasks in a workflow with minimal user actions.

26 Claims, 24 Drawing Sheets

Typical Workflow

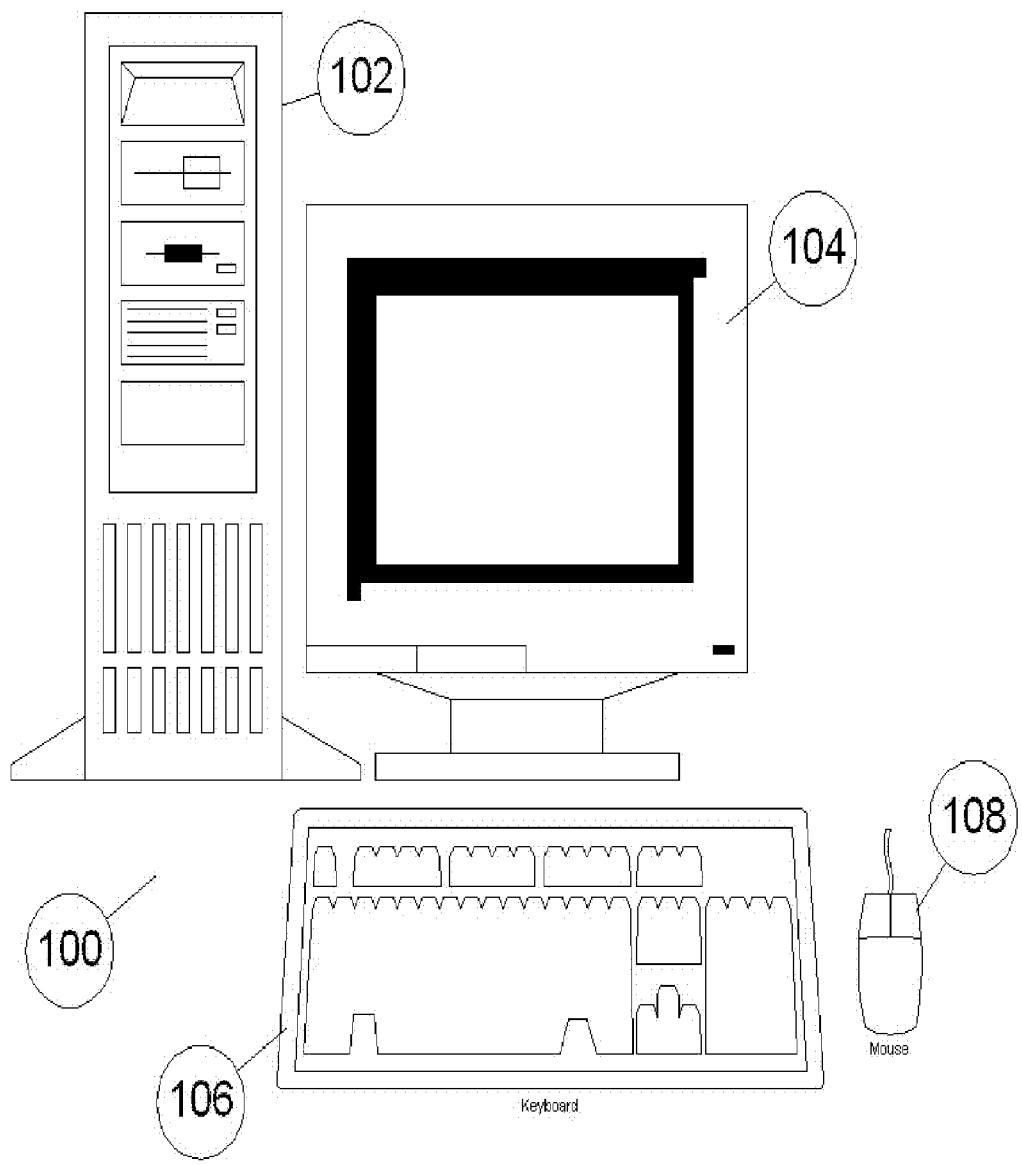
Figure 1: System drawing

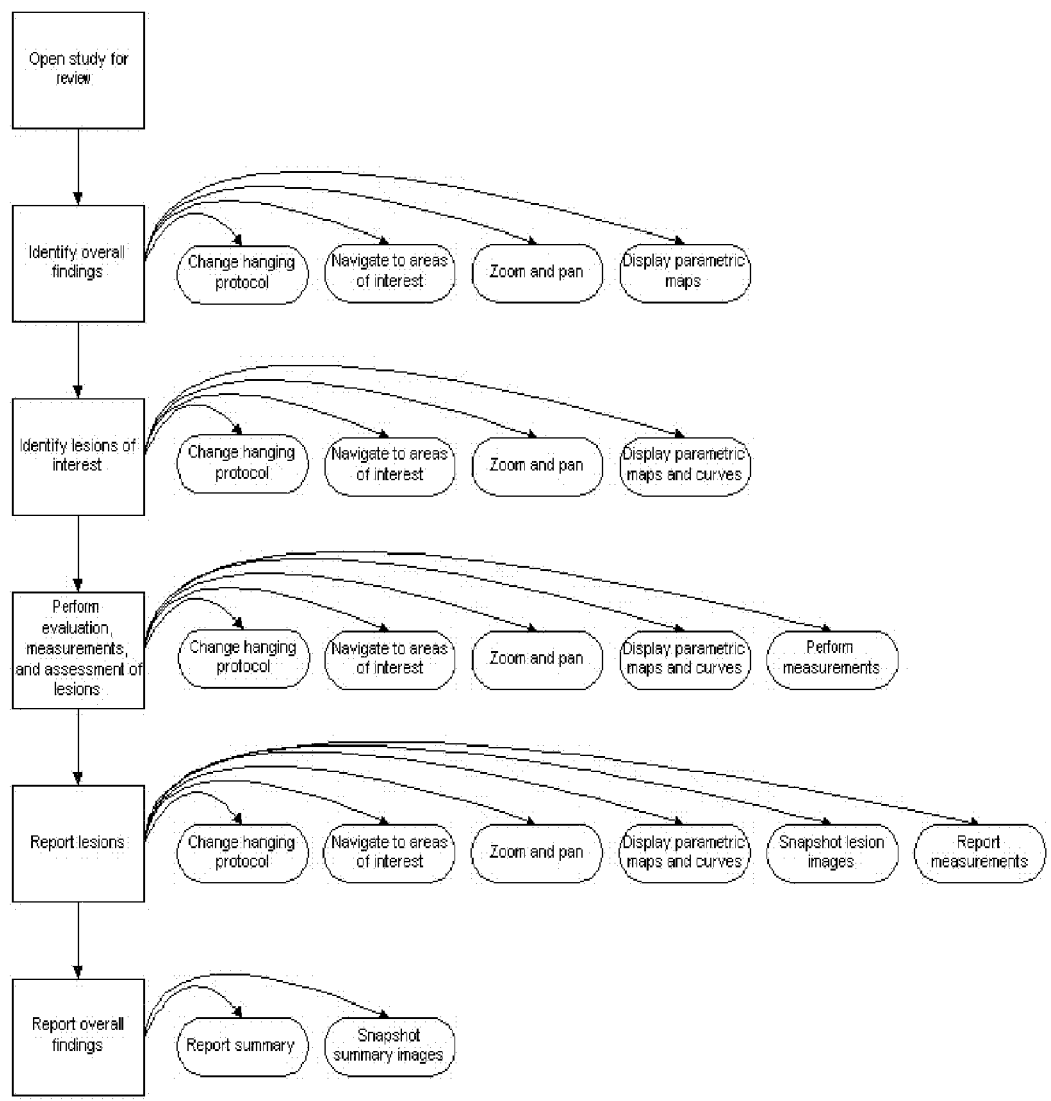
Figure 2: Typical Workflow

Figure 3: Workflow panel showing an example breast MR diagnostic workflow: Findings tab, lesion panel, and tablets for each task of evaluating and reporting lesions.

Figure 4: Workflow panel showing an example liver MR diagnostic workflow: Findings tab, summary panel, and tablets for each task of identifying and reporting overall findings.

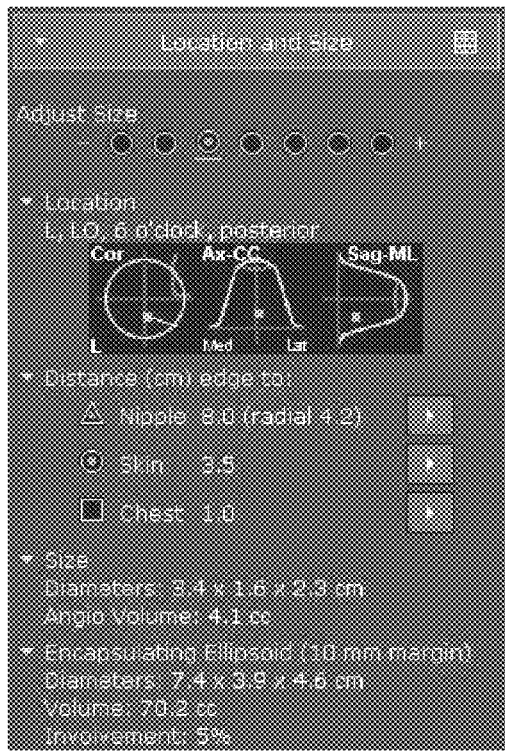
Figure 5A: Expanded tablet
Figure 5B: Collapsed tablet

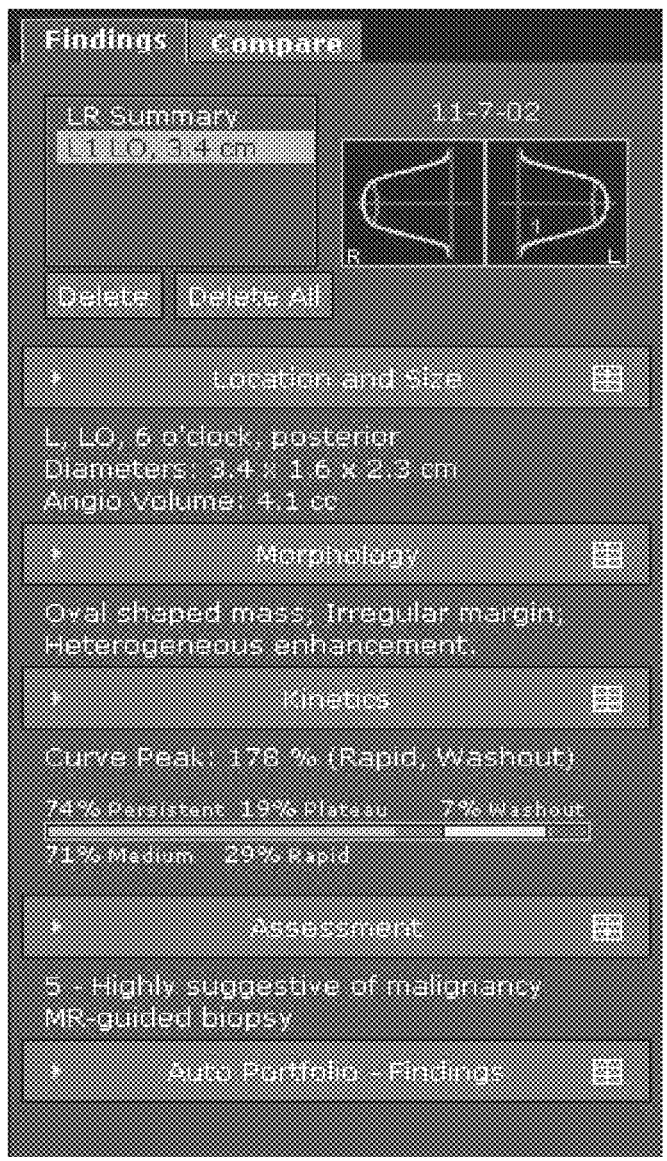
Figure 6: Findings workflow panel with all tablets collapsed (breast MR example)

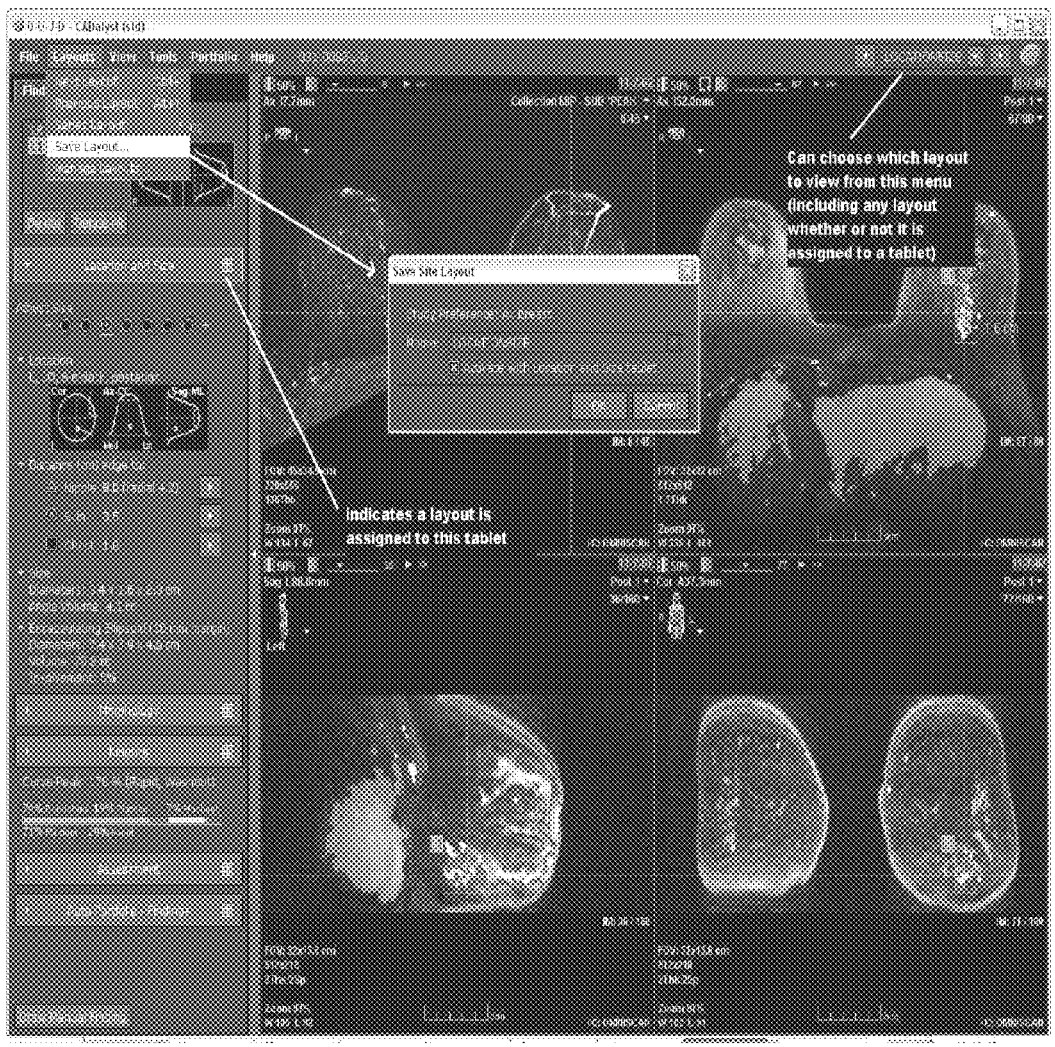
Figure 7: Save Layout menu selection and dialog

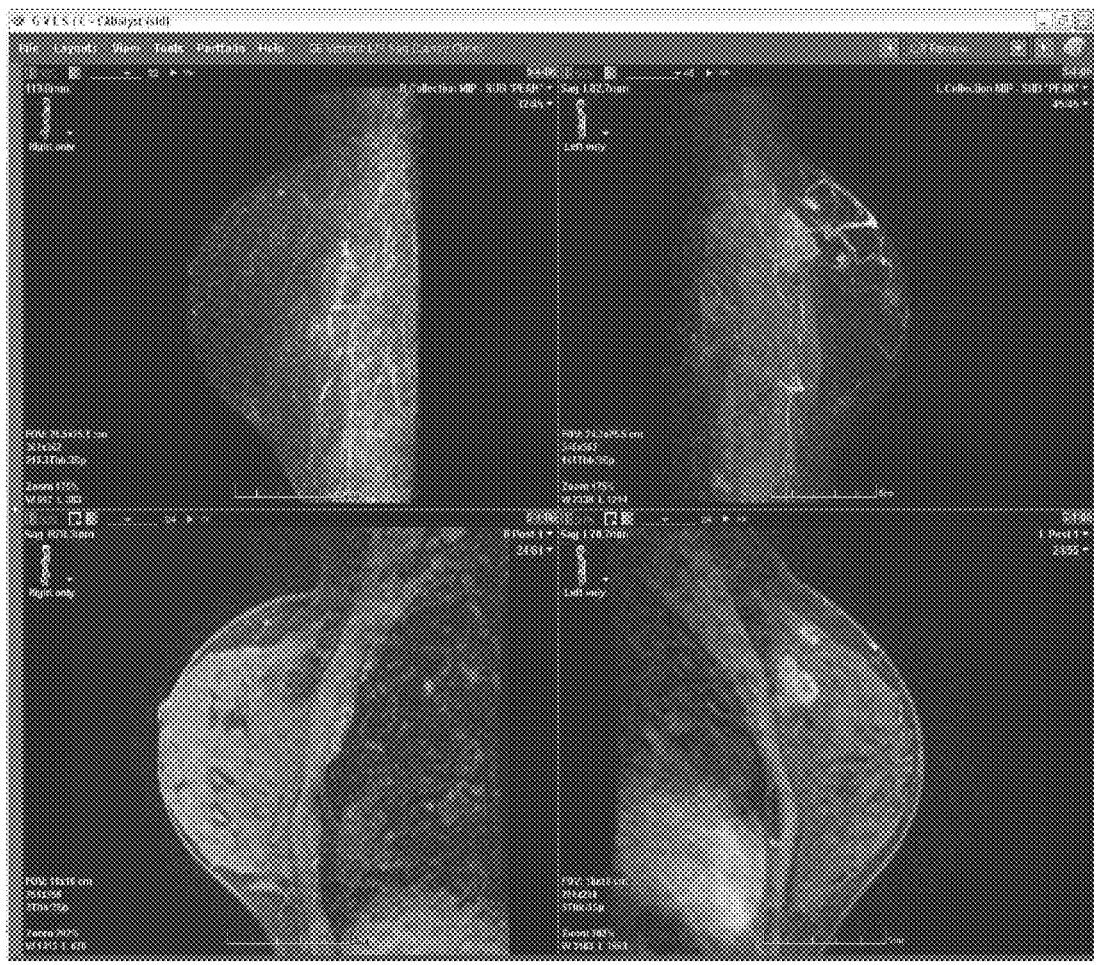
Figure 8A: Layout showing both right-only and left-only series, thus it is not switchable.

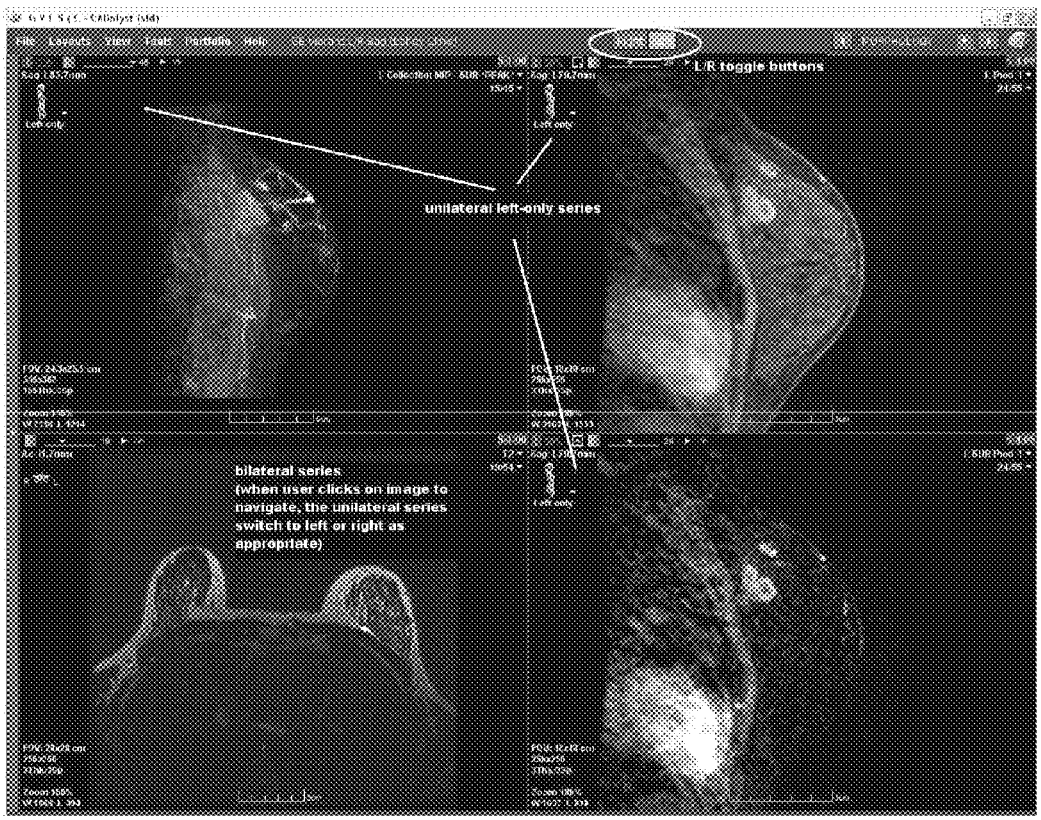
Figure 8B: Layout showing switchable unilateral series and one bilateral series. Clicking on the bilateral series to do a 3D navigation or clicking on the left/right toggle buttons may switch the unilateral series to left/right as appropriate.

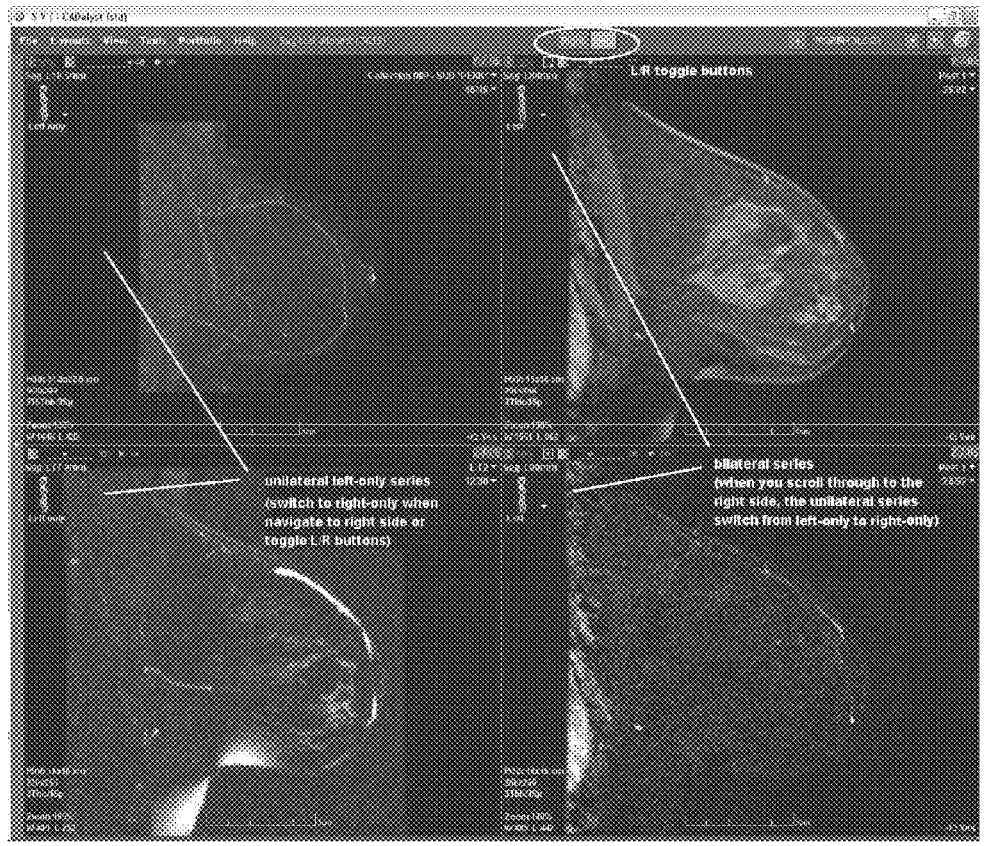
Figure 8C: Layout showing two switchable unilateral series and two bilateral series. Scrolling through the bilateral series or clicking on the left/right toggle buttons may switch the unilateral series to left/right as appropriate.

Figure 9A: Sample Images
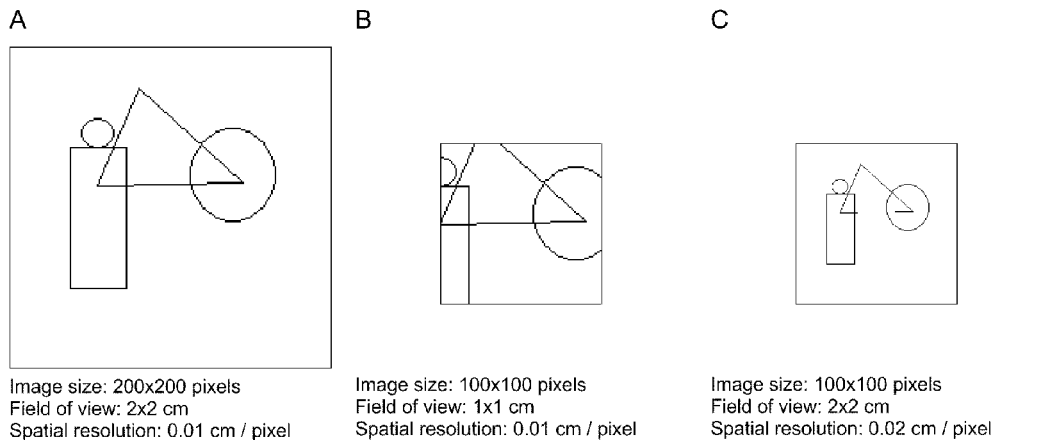

Figure 9B: Pixel zoom method
This is a typical method of zooming images. Since this type of zoom holds the ratio of the display pixels to image pixels constant, the circle appears to be a different size in image C.
Pixel zoom: 1X
A
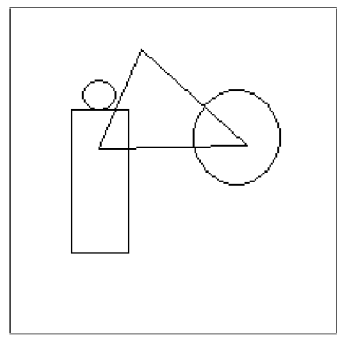
B
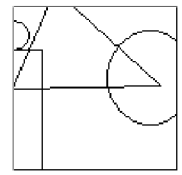
C
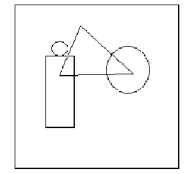
Pixel zoom: 2X
A
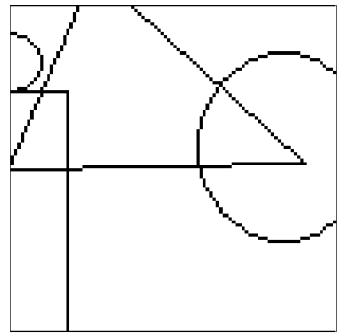
B
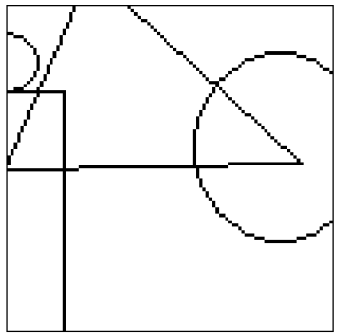
C
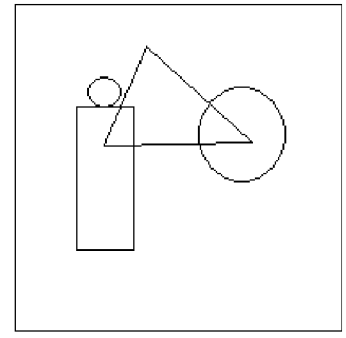

Figure 9C: Spatial zoom method

This type of zoom holds the image spatial resolution constant. Thus, image C will be zoomed to the same spatial level as image A and B. Note all features now appear the same size. For example, the 0.5 cm diameter circle appears the same size now in all images. Two sets of the three images are shown, each one at a different spatial zoom level (images are cropped as needed).

Spatial zoom: 0.01 cm / pixel

A                     B                     C

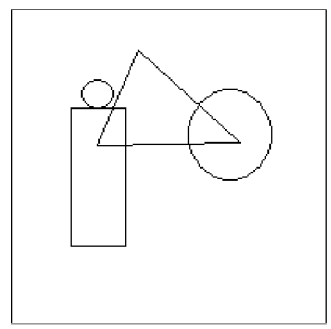 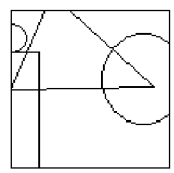 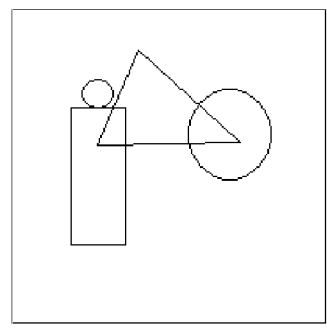

Spatial zoom: 0.005 cm / pixel

A                     B                     C

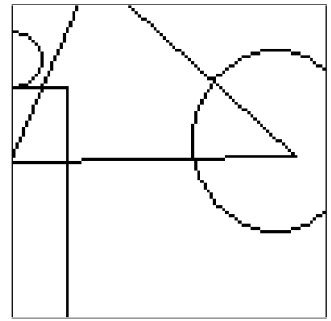 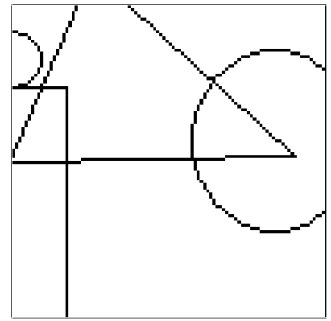 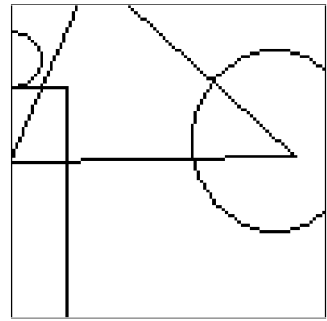

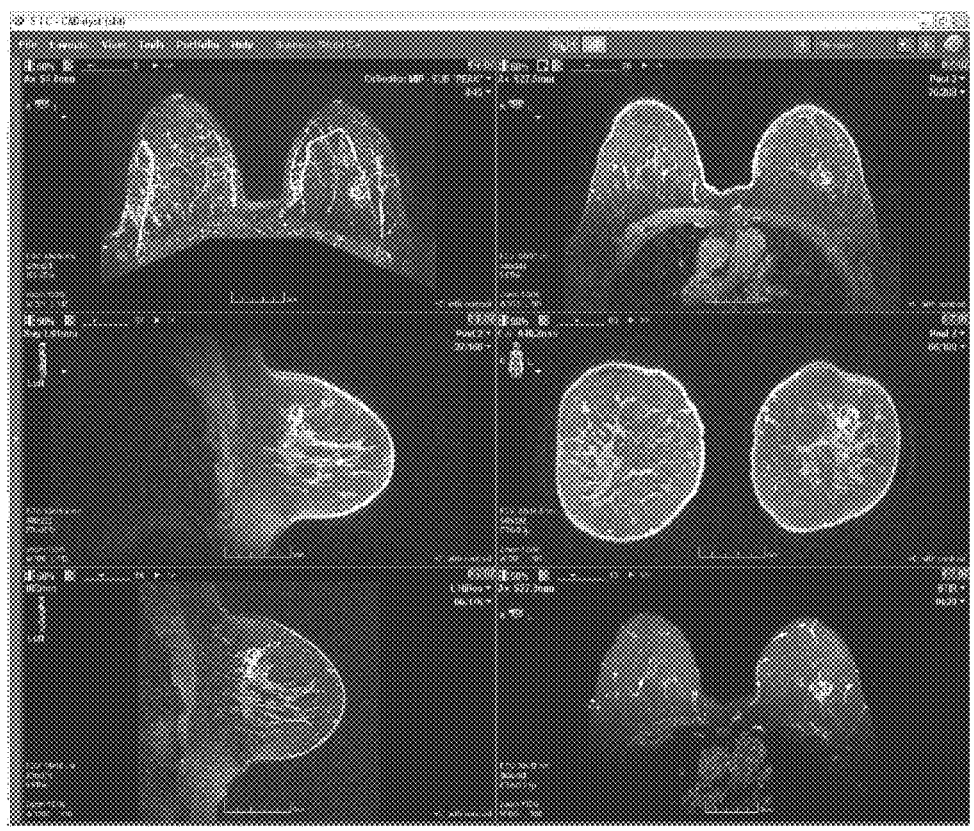
Figure 10A: Sample kinetic map overlays on a maximum intensity projection, the original temporal series (axial), reformats of the temporal series (sagittal and coronal), a high resolution acquisition, and a STIR series.

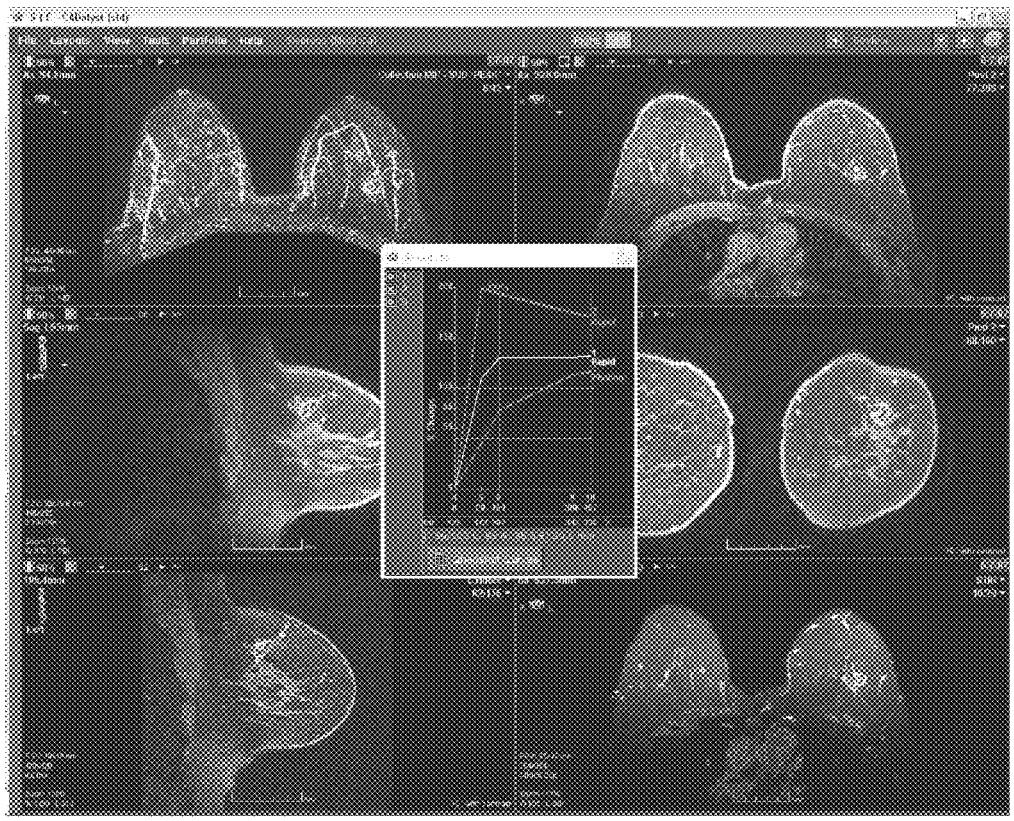
Figure 10B: Sample kinetic map overlays and kinetic curves generated based on the spatial location of non-temporal series, then transposed to the original temporal series to compute the curve

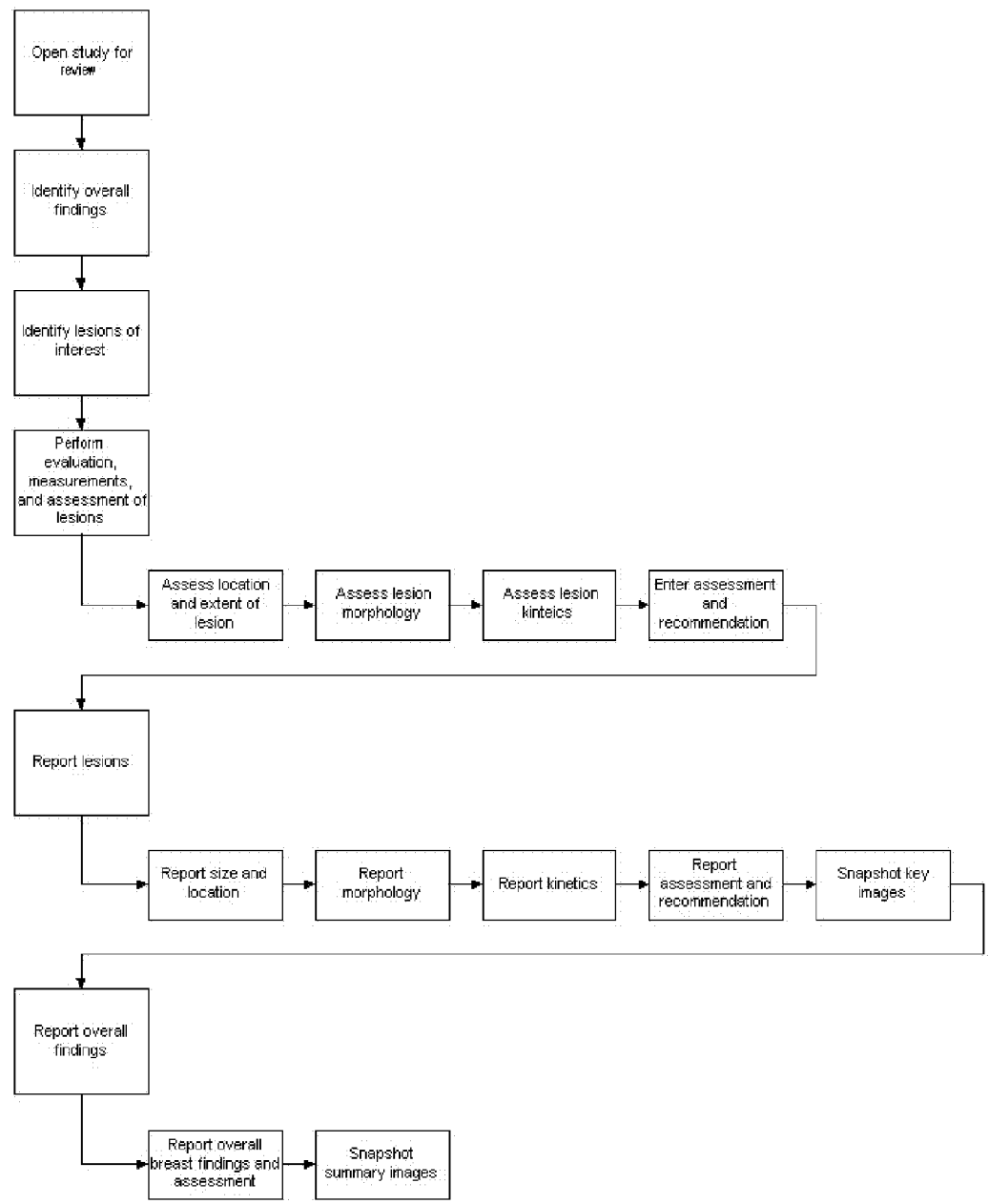
Figure 11: Breast workflow

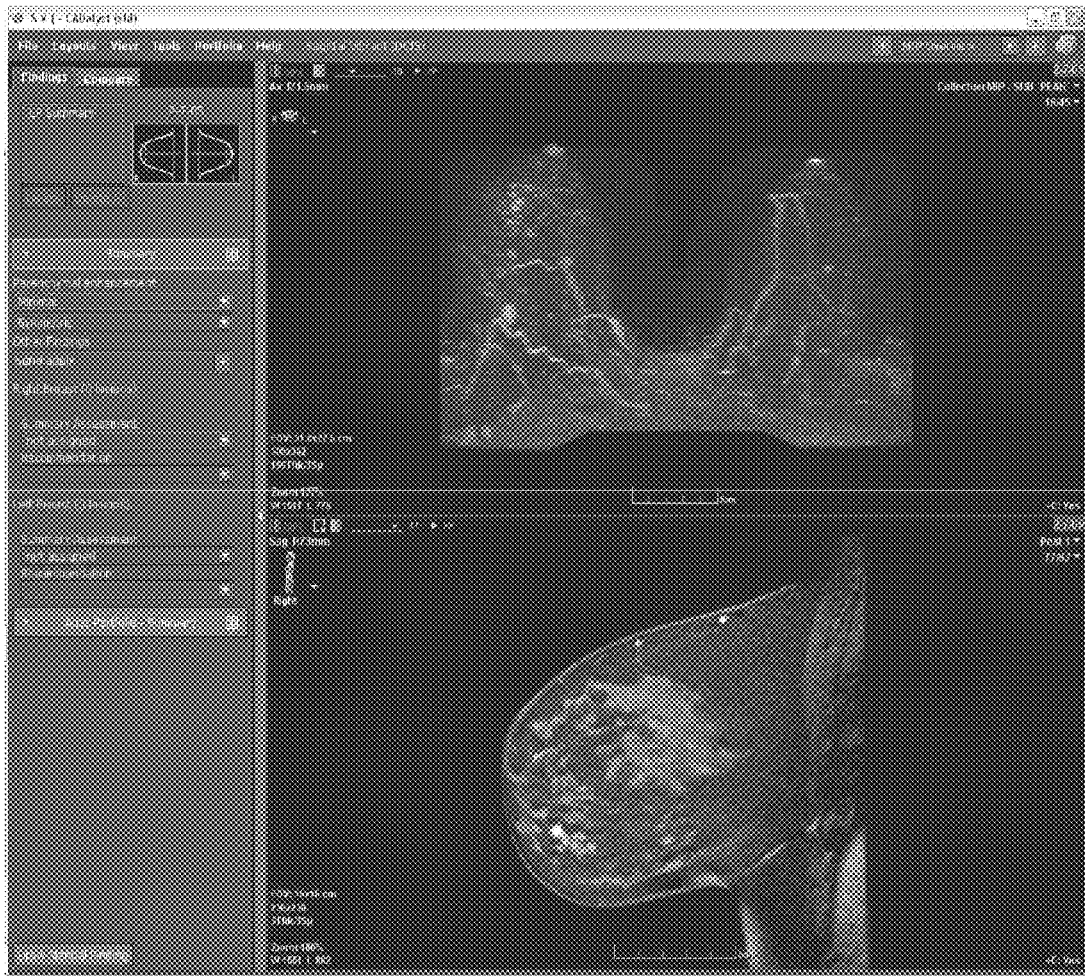
Figure 12: Breast example – Summary tablet and hanging protocol

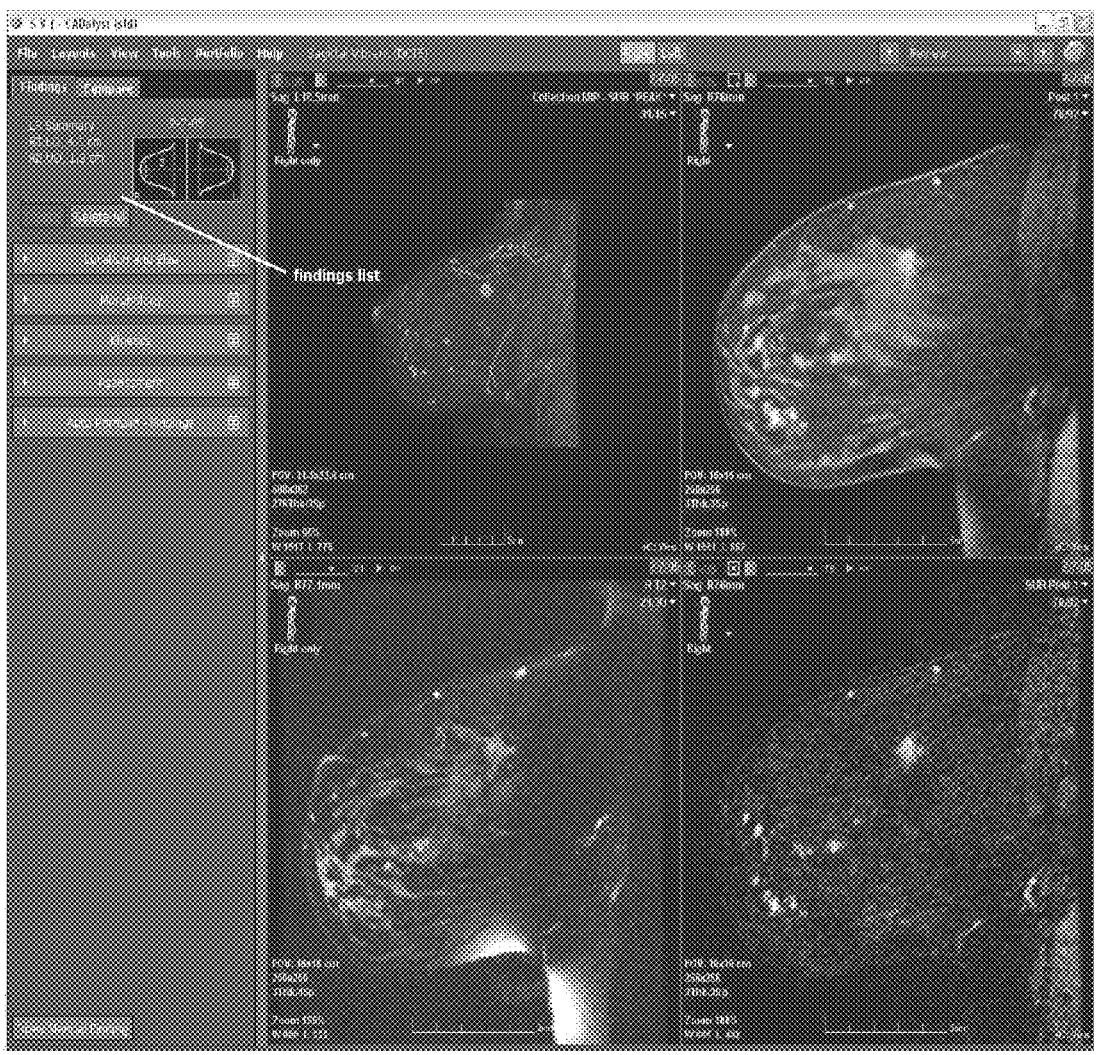
Figure 13: Breast example – Findings tab with findings list and hanging protocol for review

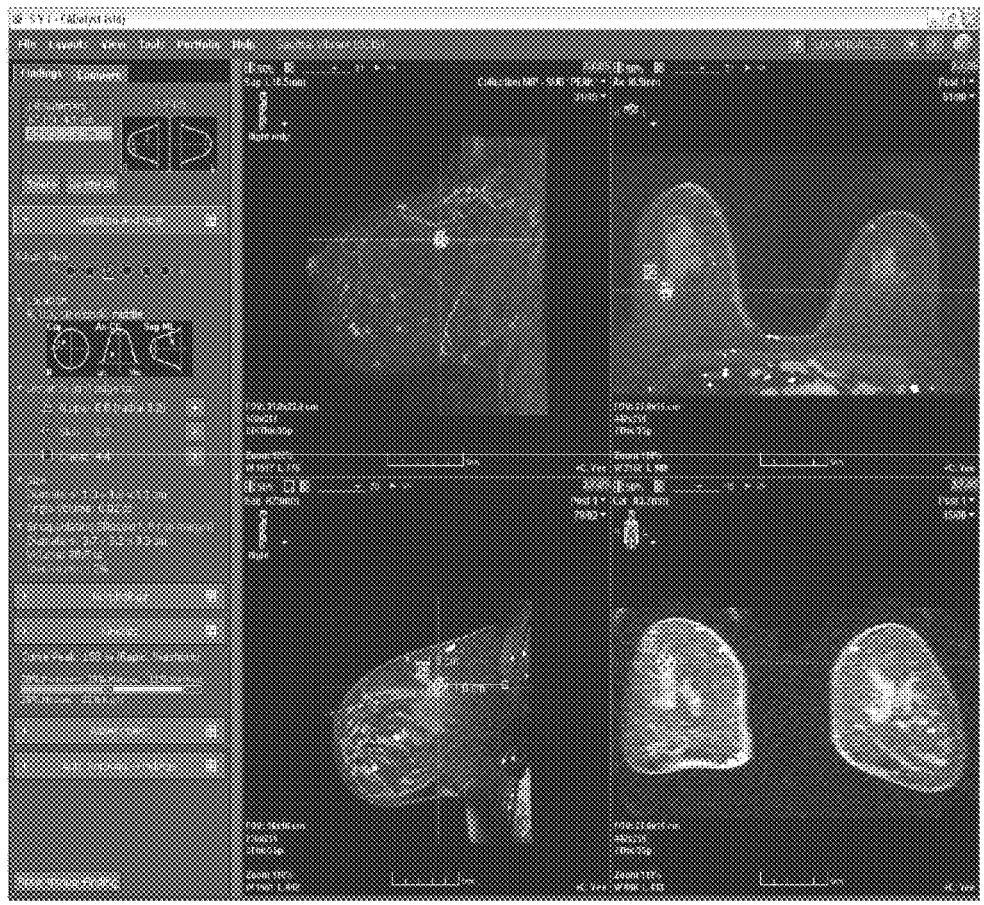
Figure 14: Breast example – Location and Size tablet with associated MPR hanging protocol

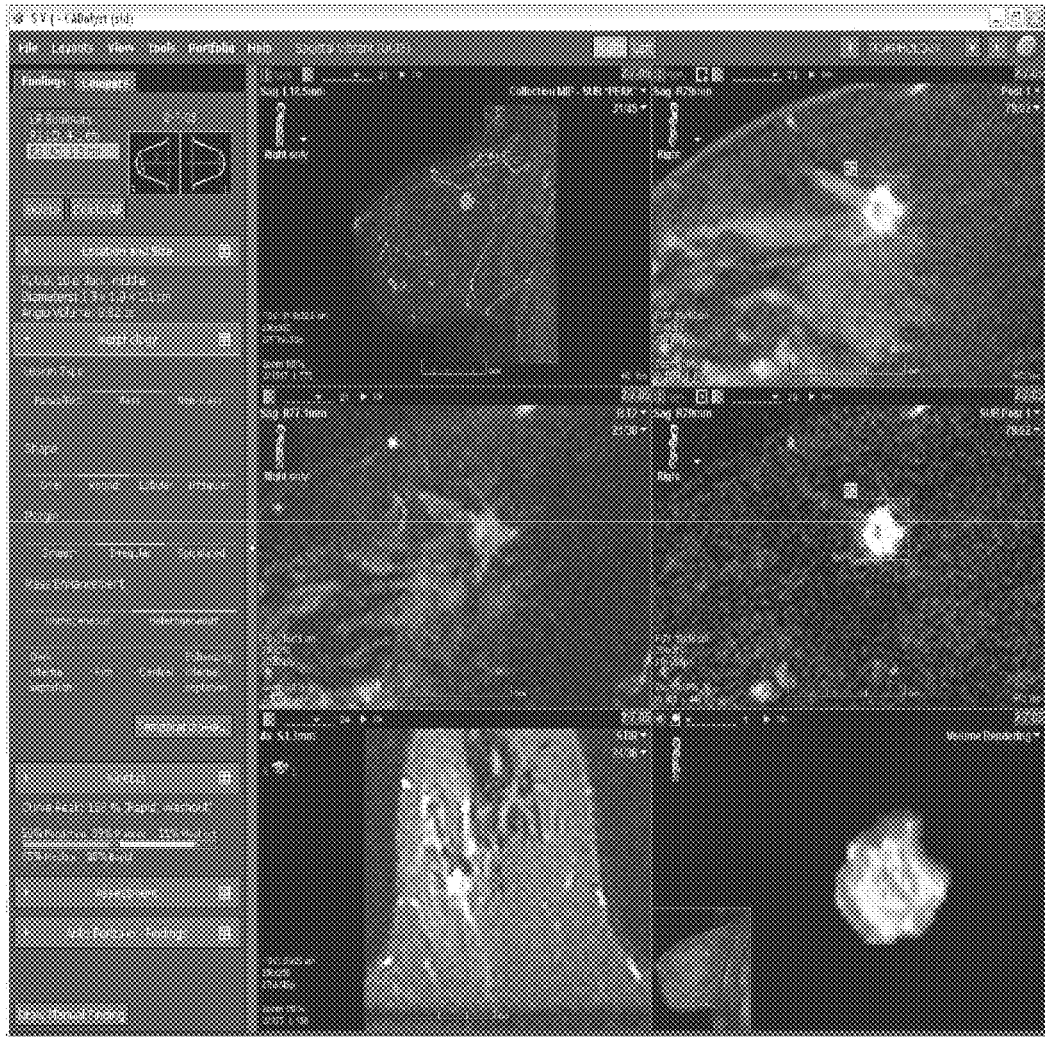
Figure 15: Breast example – Morphology tablet with associated hanging protocol showing zoomed series that depict the morphological characteristics

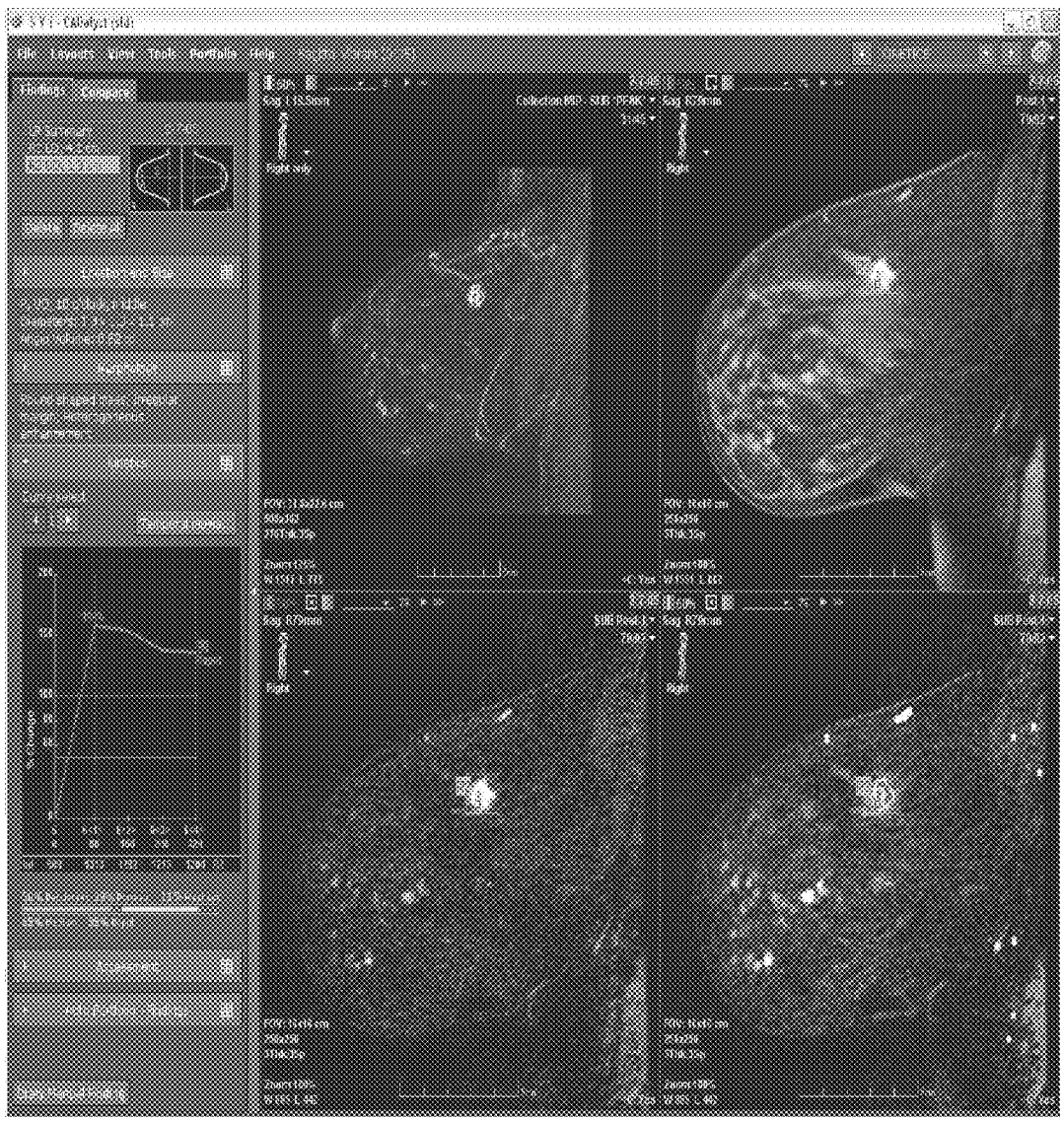
Figure 16: Breast example – Kinetics tablet with associated hanging protocol showing temporal series, subtractions, and parametric map

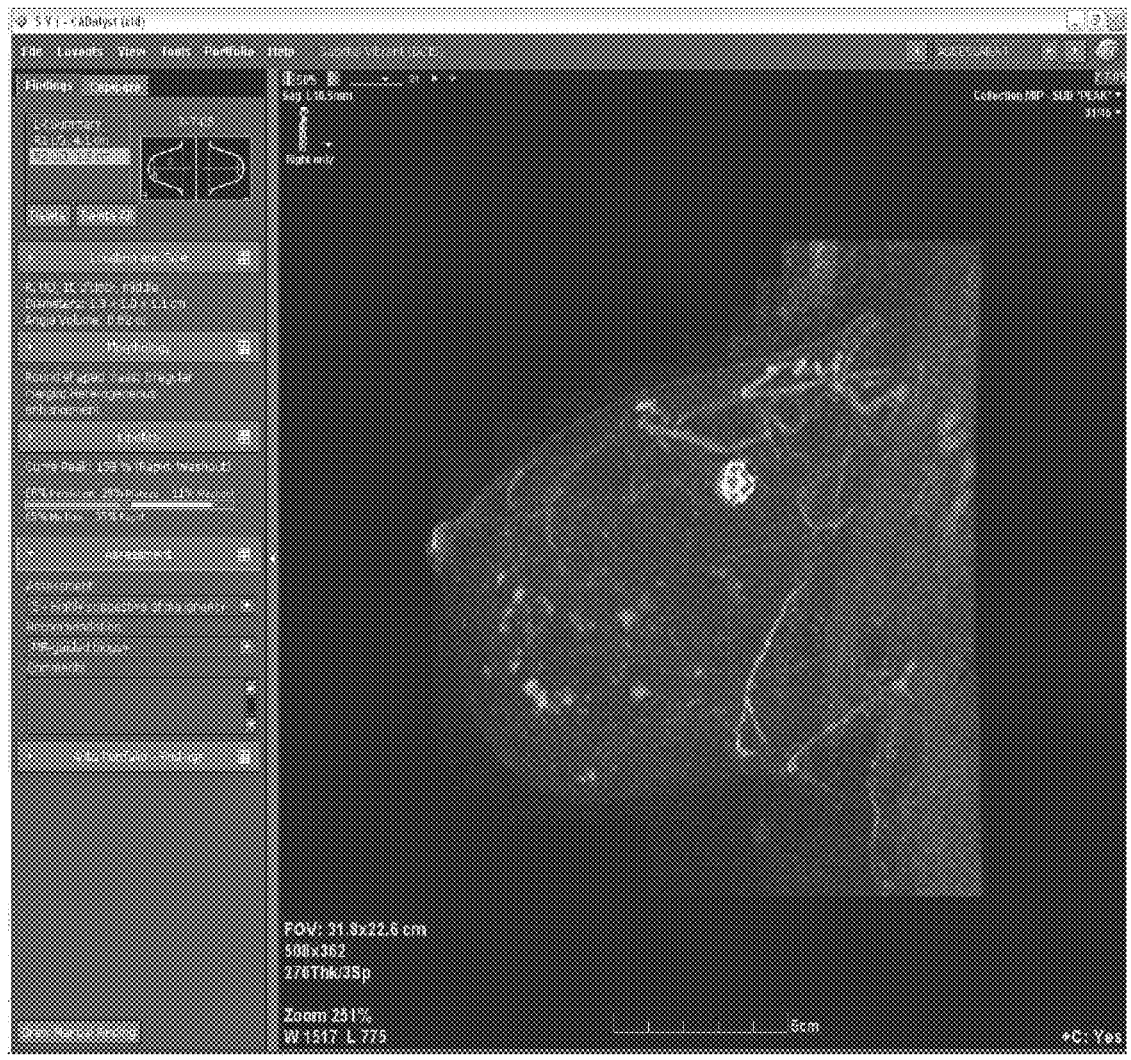
Figure 17: Breast example – Assessment tablet with associated hanging protocol showing a MIP overview image

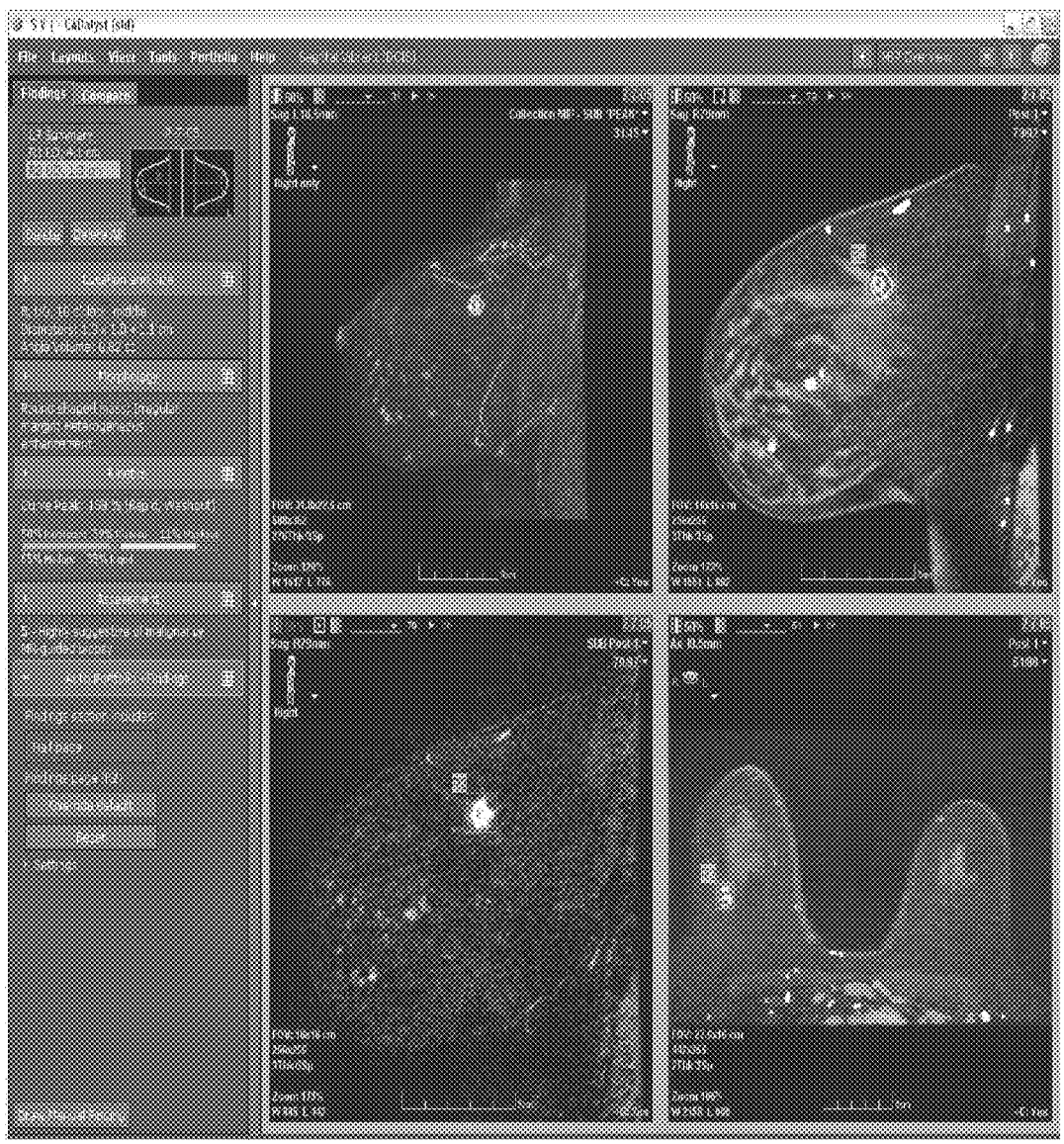
Figure 18: Breast example – Auto Portfolio-Findings tablet with hanging protocol used to automatically capture key images for the report. All other tablets are collapsed showing the information included in the report, listed in dictation order.

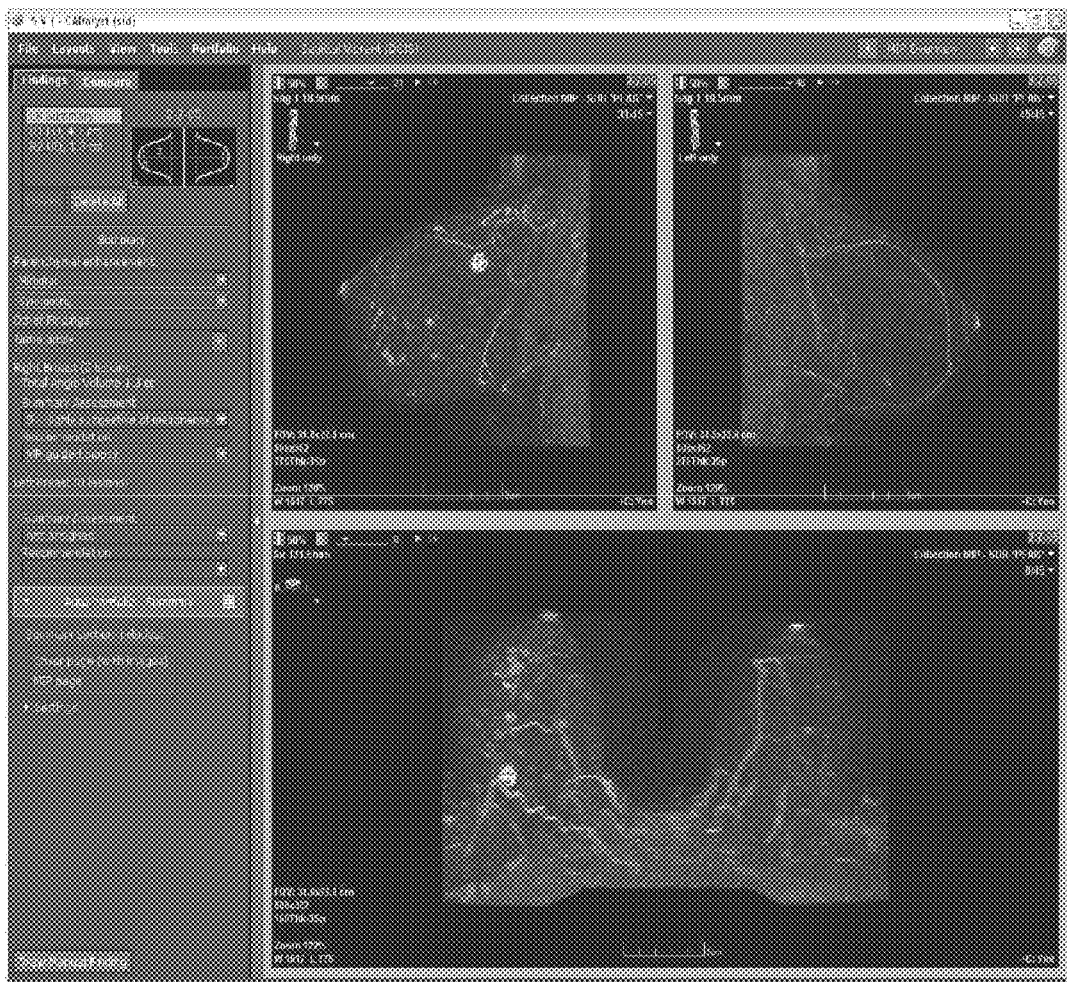
Figure 19: Breast example – Auto Portfolio-Summary tablet with MIP summary layout highlighting the list of findings, with the overall findings and summary data shown above.

SYSTEM AND METHOD FOR EFFICIENT WORKFLOW IN READING MEDICAL IMAGE DATA

BACKGROUND OF THE INVENTION

1. Field of the Invention

The present invention is directed generally to a system and method for improving workflow in reading and analyzing medical image data.

2. Description of the Related Art

There are several tools common in radiology image viewing stations that aid the radiologist in reviewing studies. Some of these include the use of hanging protocols, navigating through images, zooming and panning images, and applying parametric maps or overlays on the images. While these tools are common and do provide benefit to the users, there are several disadvantages or shortcomings to the typical implementation of these features.

Workflow. There are many radiology viewing stations that provide various tools for analyzing, measuring, and assessing findings and studies. However, most often the user is presented with a collection of tools to use, but it is up to the user to decide which tools to use when. In addition, the user is left hunting around for the various measurements, assessments, and images for each of the findings in order to summarize the study, snapshot key images, and dictate or create the report.

Hanging Protocols. It is common in radiology image viewing stations to support hanging protocols, where the user saves various layouts (including the location and size of image windows, and the series to view in each window). When reviewing studies, the user may choose the desired layout to view, or quickly cycle between the next or previous layout. However, when working through certain tasks or interactions in the software inherent in the workflow of reviewing a study, changing to a related hanging protocol is an extra action the user has to invoke.

Another issue with hanging protocols is based on reading studies where the images are acquired or split into separate unilateral series (e.g., separate left and right images). Some hanging protocols may show the left and right images side-by-side, and scroll through them together. However, some desired layouts are typically only showing one side or the other. This results in a multitude of saved layouts (one for each side), and extra actions for switching between them while viewing the study.

3D Navigation. In prior versions of CADstream, the user could click on any image and the other displayed images would automatically navigate to sync up to the same spatial location (based on the spatial positions defined for the MR images). The navigation would update the view of images from any orientation, thus it is a 3D navigation. However, often the user may then scroll through images, see another area of interest, and perhaps want to switch to display an image in an orthogonal plane (such as from a reformatted series), or the user may change the hanging protocol wanting to view that finding in other series. Typically, the user then has to navigate to the position again in the new layout, wasting time.

Zoom and Pan. Typically, images are zoomed based on the image to display pixel ratio. For example, a 1× zoom is where each pixel of the image data is shown directly as a single pixel on the display. It is also common to be able to link images in the same plane so they zoom and pan together. Problems arise when you have images of different spatial resolution (millimeters/pixel differs), or different field of view (image spatial size may vary). It can be difficult to get them to zoom such that the feature of interest is displayed as the same size in all images, yet it is confusing when they are displayed differently. There is also time wasted by the user panning the images so the area of interest is in the viewable area as images are zoomed.

The zoom and pan properties are typically saved in the hanging protocols as well. However, when the zoom is tied to the display pixel size, the actual area of the image shown will vary when switching between different display stations that have different screen resolutions (display pixel sizes). Rather, the user is typically most interested in zooming to show a desired field of view within the window. Thus, the saved zoom in the layouts are not ideal in all situations.

Parametric Maps. When reviewing MR studies for cancer, often the user evaluates the kinetic behavior of dynamic or temporal series. In addition, users evaluate the image characteristics in other non-temporal series. Thus, the user often needs to correlate the kinetic behavior to a specific location on these other series. It is common to display a parametric map or overlay computed to represent the kinetic behavior on temporal images. However, the non-temporal series are often acquired in a different field of view, slice thickness, and/or orientation, making it difficult to quickly identify the kinetic behavior at the same location as an area of interest on the non-temporal series.

BRIEF DESCRIPTION OF THE DRAWINGS

FIG. 1 illustrates an exemplary computer system used to analyze medical imaging data in a manner described herein.

FIG. 2 illustrates a typical workflow for medical image analysis and review.

FIG. 3 is a screen display illustrating a workflow panel showing an example breast magnetic resonance diagnostic workflow.

FIG. 4 is a screen display illustrating an example workflow panel showing an example liver magnetic resonance diagnostic workflow.

FIG. 5A is a screen display illustrating an expanded tablet.

FIG. 5B is a screen display illustrating a collapsed tablet version of the display of FIG. 5A.

FIG. 6 is a screen display illustrating a findings workflow panel for breast magnetic resonance image with all tablets collapsed.

FIG. 7 is a screen display illustrating how to save hanging protocols, and how to choose them for display.

FIGS. 8A-8C are screen displays of medical image data shown on a display and illustrating left/right split layouts in medical image data.

FIGS. 9A-9C illustrate the effect of image and screen resolution as it relates to a zoom operation.

FIGS. 10A-10B are screen displays illustrating medical image data and the overlay of kinetic map data, respectively.

FIG. 11 illustrates an example workflow diagram for breast imaging analysis and review.

FIG. 12 is a screen display illustrating a summary tablet and hanging protocol for the breast image analysis in the workflow of FIG. 11.

FIG. 13 is a screen display illustrating a tablet with findings list and hanging protocol for the breast image analysis in the workflow of FIG. 11.

FIG. 14 is a screen display illustrating a location and size tablet and hanging protocol for the breast image analysis in the workflow of FIG. 11.

FIG. 15 is a screen display illustrating a morphology tablet and hanging protocol for the breast image analysis in the workflow of FIG. 11.

FIG. 16 is a screen display illustrating a kinetics tablet and hanging protocol for the breast image analysis in the workflow of FIG. 11.

FIG. 17 is a screen display illustrating an assessment tablet and hanging protocol for the breast image analysis in the workflow of FIG. 11.

FIG. 18 is a screen display illustrating an auto portfolio findings tablet and hanging protocol for the breast image analysis in the workflow of FIG. 11.

FIG. 19 is a screen display illustrating an auto portfolio summary tablet and hanging protocol for the breast image analysis in the workflow of FIG. 11.

DETAILED DESCRIPTION OF THE INVENTION

FIG. 1 illustrates an exemplary system 100 for reading radiologic studies, comprising a personal computer (PC) 102, monitor 104, keyboard 106, and mouse 108. The PC 102 also includes conventional components such as a disk drive, optical storage, memory, interface components, such as a network interface, and the like. For example, the medical image data may be stored on a network storage device and coupled to the PC 102 via the network interface. The operation of the PC 102 is well known in the art and need not be described in detail herein.

As will be described below, the workflow of the present disclosure is directed to a technique for efficiently displaying medical imaging data for the radiologist or other medical practitioner to review and analyze medical image data. For a particular workflow, such as breast magnetic resonance imaging analysis, a series of panels with tablets are opened for the medical practitioner. At each tablet, panels are available for additional data that is automatically displayed upon activation by the user. The additional data allows for efficient diagnosis in the selection of data and images for inclusion in a report. As each tablet is closed, summary data for that tablet is provided for the practitioner. Subsequent tablets and workflow panels are opened and completed by the user. At the end of the workflow process, the collapsed tablets, with summary information are displayed for the user to assist in the simple generation of a report without having to return and open each individual panel and tablet to extract the desired data. As a result of the workflow process described herein, the user can analyze medical image data. In addition, as the user progresses through the workflow, the user may have certain individual preferences as to workflow display and the retention of certain types of data. The analysis system constructed in accordance with the present teachings allows the creation of hanging protocol templates that can be used in the analysis of subsequent medical image data so that reports have consistent appearance and the inclusion of data selected preferentially by each user.

A typical workflow for reading a diagnostic radiologic study looking for lesions is shown in FIG. 2. The steps of the workflow include:

1. Open study for review.
2. Identify overall findings. Typically, radiologists start by getting an overall impression of the study. This may include things such as the background parenchymal enhancement or amount of fatty tissue, the health of other organs in the view, and possibly a first impression or characterization of the lesions in the study. To do this, they may select various hanging protocols to view the desired images, navigate through the images and to areas of interest, zoom and pan to get a clearer view of areas, and display parametric maps.
3. Identify lesions of interest. As radiologists continue to review the study, they will identify lesions of interest or areas that need further interrogation. During this review, they may select various hanging protocols to view the desired images, navigate through the images and to areas of interest, zoom and pan to get a clearer view of areas, and display parametric maps and kinetic curves. The radiologist may evaluate various series of images obtained from different imaging modalities, such as x-rays, magnetic resonance (MR) images, or the like. As those skilled in the art will appreciate, the term "series" refers to a set of images that are obtained in a specific imaging modality. For example, one series of MR images may be obtained as part of a contrast imaging where data is collected prior to the introduction of a contrast agent and periodically measured as the contrast agent is taken up by the tissue. Another series may comprise $T_1$ or a $T_2$ image evaluations. A number of other known imaging techniques may be used to generate a series of images for evaluation. Typically, each series comprises a set of image slices that correspond to some cross-sectional area of the patient. With the efficiencies produced by the workflow process described herein, the user may rapidly select various series of images and move to the desired image slice within each series.
4. Perform evaluation, measurements, and assessment of lesions. As the list of lesions is identified, the radiologists interrogate further to determine the extent or size, the morphology, and perhaps the kinetic behavior of the lesion. Finally, they will make an assessment of the lesion indicating a diagnosis and recommendation. During this process, the radiologist may select various hanging protocols to view the desired images including reformats in other planes, zoom and pan to get clearer views, and display parametric maps and kinetic curves to assess the kinetics of the lesion of interest. A key component of this is to be able to quickly navigate to the area of interest while changing the viewed series, zoom level, and overlay displays. In addition, the radiologist will use tools to measure the lesion and its location relative to landmarks.
5. Report lesions. Once the lesions have been identified, quantified and assessed, the radiologist reports the findings. This typically includes snapshots of key images, the size and location measurements, evaluation of the morphology and kinetics, the clinical assessment and recommendation. To do this, the radiologist may select different series to view, or again select the desired hanging protocol and navigate to get the view desired for reporting (such as the one containing the measurements) or capturing other key images. The user may also annotate the images with comments or measurements. The system 100 allows users to save a hanging protocol setup, so when reading studies, they just choose the desired saved hanging protocol, and the appropriate images appear as specified in the configuration for that hanging protocol.
6. Report overall findings. Finally, any overall findings are reported, including some snapshot images showing the summary of the findings. Again, this may require changing hanging protocols and navigating to the desired views.

The workflow described above is typical for diagnosis. However, in many studies, the user compares some of the findings in the current study with a prior study. So, there may be multiple workflows in an application, such as the diagnostic workflow and the comparison workflow. Each step of a workflow consists of one or more tasks to perform. For example, in a liver study, the user may assess the abdomen and the liver as two tasks within step 2 (i.e., identify overall findings). Within step 4 (i.e., perform evaluation, measurements, and assessment of lesions), the user may have several tasks, such as determine the location and size of the lesion, assess the morphology, and evaluate the kinetics of the lesion. To accomplish a given task, the user may perform several actions, such as changing series and images to view, zoom, pan, view the parametric maps, etc. Those actions are shown in the bubbles branching from some of the steps in FIG. 2.

The present disclosure covers many aspects of workflows that make it extremely efficient for the user as they progress through the tasks within a workflow. In particular, this is significant as you monitor the user actions, such as the amount of mouse movements and the number of mouse clicks. The present system requires minimal actions to accomplish the tasks in the workflow as compared to the actions required for those same tasks on other systems.

There are some aspects of this disclosure that are used in all of the steps of review. In particular, the workflow panel, use of hanging protocols, zoom and pan, navigation, and display of parametric maps are used throughout the review process. The operation of each of these are described, followed by an example workflow showing how these are utilized in conjunction resulting in a fully optimized workflow. The examples discussed herein are based on diagnostic MR workflows. However, those skilled in the art will appreciate that the present teachings are not limited to MR studies, and in fact part of the workflow efficiency is indeed determining the specific workflow for a particular study type, and adapting these principles accordingly.

Workflow Panel. An initial process is to create a workflow panel which will organize the tasks within the workflow. The workflow panel may include multiple tabs if there are multiple workflows for that application, such as the diagnostic/findings workflow and the comparison workflow. Within each workflow tab, there may be multiple panels for groups of tasks within that workflow. For example, there may be a summary panel used to identify and report the overall findings, and a lesion panel used to identify, evaluate, and report the lesion findings. The workflow panel may also include tablets corresponding to tasks within the workflow. The tablet contains the data and tools relevant to the task, and the user also has the option of saving a hanging protocol that will automatically be displayed when the tablet is selected. For example, when reading diagnostic breast MR, the user will typically scroll through the images looking for areas of interest. Once an area is found, the user will interrogate the lesion, assessing the morphology and kinetics. If it is worthy of reporting, the user will ensure the location and size of the lesion is correctly reported, enter the assessment and recommendations, and report the finding. FIG. 3 provides an example breast MR diagnostic workflow panel. At the top, there are tabs for each workflow (a Findings tab for the diagnostic workflow and a Compare tab for the comparison workflow). In the findings tab is a lesion panel and the set of tablets depicting each task to perform while evaluating and reporting the lesion. In the example of FIG. 3, there are tablets available for "Location and Size," "Morphology," "Kinetics," "Assessment," and "Auto Portfolio—Findings." One skilled in the art will appreciate that different tablets will be made available for different tasks within each workflow panel.

Another workflow panel example is shown in FIG. 4. It shows a liver MR diagnostic workflow panel with the findings tab (diagnostic workflow) and summary panel with tablets depicting each task to perform while identifying and reporting overall findings. In the example of FIG. 4, the liver diagnostic workflow panel includes tablets for "Abdomen," "Liver," "Segmentation," and "Portfolio" to indicate the tasks for this particular workflow panel.

Though these screens of FIGS. 3 and 4 show the workflow panel on the left side, it could be displayed in other areas of the screen (such as the bottom, top, or right side). This panel is designed like a "drawer" where the user may click anywhere along the left border to open the panel for display, and then click again to close or hide it.

The user interface includes tablets that the user may select for each of the tasks specific to the workflow for that study type. Many tablets can be expanded or collapsed. When a tablet is selected, it is expanded revealing all of the associated data and tools. When a tablet is collapsed, just the key data are shown for quick reference and reporting purposes. For example, in breast MR studies (see FIG. 3), a Location and Size tablet is available for assessing and reporting the location and size of a lesion. The expanded tablet (see FIG. 5A) shows the location of the lesion relative to the breast landmarks, distances to landmarks, and the size of the lesion. Tools are available when the tablet is expanded for adjusting the reported location, editing the size of the lesion, and quickly navigating to the relative landmarks and editing the distances of the lesion's edge to those landmarks. When the tablet is collapsed (see FIG. 5B), the key location and size information is displayed. This provides a quick display of the measurements to be included in the report for dictation or reference.

The user progresses through the tasks in the workflow, interrogating the finding and entering the desired data for the report. Finally, when reporting the lesion, the collapsed display of each tablet shows all of the key data for easy dictation or inclusion in the report (see FIG. 6).

Hanging Protocols. The process described herein provides the user the ability to associate a custom hanging protocol, or layout, with a tablet (task) in the workflow panel of the user interface. For example, when assessing the morphology, the user could save a custom layout that would automatically show the series used to assess morphology, plus automatically zoom in the images around the lesion for a clearer view. This saves considerable time, since the user otherwise would have to also go change the viewed series or change the layout, then zoom and pan the images to assess the morphology. When assessing the kinetic behavior, the user may save a custom layout that highlights the kinetics, including images from the temporal series, subtractions, and the parametric overlay. Again, a single click shows the kinetic data in the user interface, as well as changing the hanging protocol to show the optimal view for assessing kinetics in the images. When determining the size and location of the lesion, a multi-planar reformat (MPR) image view is most useful since the user can easily see the lesion in all orthogonal planes. Finally, when reporting the lesion, all of the key data are shown in the collapsed tablets, and a corresponding layout that includes the desired images for summarizing the lesion can be shown and included in the report. This streamlines the workflow for the user, and greatly reduces the amount of time spent changing series to view and zooming and panning.

In this system, the user can easily setup each of these hanging protocols. First the user arranges the screen in the desired view. This includes the number of image areas to display, the series in each image area, whether the parametric overlay is displayed, the zoom level, and any other image settings used by the application. In addition, the user sets the workflow panel to be hidden, or open for display with the associated tablet selected. When the display is setup the way the user wants it saved, the user simply selects the Save Layout . . . option from the Layouts menu. A dialog then allows the user to name the layout and optionally assign it to the current tablet (see FIG. 7). If the user chooses to associate it with a tablet, an icon is shown on the tablet indicating there is an assigned layout, and then any time the tablet button is chosen, the saved hanging protocol will be displayed. At any time, the user can choose any of their saved hanging protocols for display from the layout chooser at the top right of the screen.

The customized settings for each hanging protocol designated by the user may be stored in the memory (not shown) of the PC 102. In one exemplary embodiment, the hanging protocol settings, customized for each work panel, are saved in association with the specific report for each patient. In another exemplary embodiment, the radiologist may specify customized hanging protocols associated with the workflow prior to opening any data file for a specific patient. In this manner, the hanging protocols for each work panel will be automatically associated with the patient data files thereby simplifying the analysis process for the user. When the reports are subsequently saved, the hanging protocol customized settings are saved in association with that newly-generated report.

Unilateral Hanging Protocols. Another feature of the hanging protocols is better support for unilateral series (separate left and right images). This is particularly useful in breast imaging where it is somewhat common to scan and/or view each side as separate series in the sagittal plane. The system 100 is designed to recognize series that are split into left and right sides even though they are otherwise the same series type. Examples are a left and right T2-weighted series or left and right dynamic series. In some cases, based on the user's configuration, the system 100 actually performs the splitting of a single series into the separate left and right counterparts as desired by the user. When a study has split left and right series, it doubles the number of series to view, and typically doubles the number of hanging protocols for the user to manage (since there would be two layouts saved for each desired hanging protocol—one for the left side and one for the right side).

In accordance with the system 100, when the user saves a hanging protocol that includes unilateral series of the same laterality (i.e., all left or all right), the system uses that single layout to display either side. The system determines whether a hanging protocol is left/right switchable based on the following logic: For each series in the hanging protocol, if the series is unilateral AND has a left/right counterpart series, that layout is marked as switchable. Thus, if any one of the series in the hanging protocol is a left-only or right-only series, and if that series has a right/left counterpart, then the hanging protocol is left/right switchable. When the system determines that the hanging protocol is switchable, a button is shown which allows the user to easily switch between the left and right sides. Clicking on the "right" button will toggle all left-side series to their right-side counterpart series. Clicking on the "left" button will toggle all right-side series to their left-side counterpart series. See FIGS. 8A-8C for some example switchable layouts. FIG. 8A illustrates a layout showing both right-only and left-only series. Thus, the data in FIG. 8A is not switchable. FIG. 8B is a layout showing a switchable unilateral series and one bilateral series. Clicking on the bilateral series to do a 3D navigation or clicking on the left/right toggle buttons may switch the unilateral series to left/right as appropriate. The layout of FIG. 8C illustrates two switchable unilateral series and two bilateral series. Scrolling through the bilateral series or clicking on the left/right toggle buttons may switch the unilateral series to left/right as appropriate.

The system 100 also includes automatic switching of the displayed series during the study review. There are some cases where some of the series in the layout are bilateral, and some are unilateral. In these cases, as the user navigates through the bilateral series, the unilateral images are automatically updated to reflect the current side being viewed. In addition, as a user selects a lesion, the unilateral series are automatically updated to correspond to the location of the lesion (left or right side).

Thus, the system 100 makes handling unilateral series so much simpler and efficient for the user. First, the user saves fewer hanging protocols, since they don't need to specifically save separate left and right layouts. Second, while viewing the study, the series are updated automatically based on the current spatial focus point (left or right), thus saving the user from having to switch hanging protocols manually.

3D Navigation. A key time savings when switching hanging protocols or series to view is to keep the area of interest in focus. The system 100 (like some other image analysis systems) allows the user to click on any image to perform a 3D navigation, which syncs up all of the displayed images to the location of interest. In addition, when generating a maximum intensity projection (MIP) image, a map is created that saves the spatial location corresponding to each maximum intensity pixel that was used to create the MIP image. This allowed users to click on a point in the MIP image, and the software would retrieve the spatial location from the map that corresponds to the chosen pixel, and then navigate the other images to that location. In other systems, when the user chooses a different series or hanging protocol to display (especially one with a different orientation), the user has to scroll or navigate to the point of interest again to get all of the newly displayed images synchronized to the location. However, the system 100 also keeps that position (the 3D navigation point) live and updates it as the user scrolls through the various images, zooms to a location, selects an object in the image, or otherwise changes the point of focus. Thus, as the user reviews the study, the 3D navigation point is constantly updated to the current spatial focus point, so a subsequent series or layout change will still result in syncing to that new location. The spatial focus point is a 3D navigation point, thus containing X, Y, and Z spatial coordinates. These coordinates may correspond to the left/right, anterior/posterior, and superior/inferior directions of the anatomy in the viewed images. Some user actions will set the specific 3D location, while other actions may only update one direction of the location. For example, when a user clicks on a point in an image, the entire 3D spatial location can be determined for that pixel, so the 3D navigation point is set accordingly. Similarly, when the user centers a location in a zoomed image, the 3D navigation point is updated to that spatial focus point within the zoomed image. However, when the user is just scrolling through images in a series, only the coordinate vector corresponding to the direction of scrolling gets set. For example, if the user is scrolling through a sagittal series, the direction of scrolling is left/right through the anatomy. Thus, only the X coordinate, or the left/right position, is updated as the user scrolls through those sagittal images.

When the hanging protocol includes zoomed images, they are automatically panned to ensure the 3D navigation location is in the view. This provides additional efficiency, as the user performs the various tasks in their workflow without losing their spatial focus point. Thus, the user can click on a finding, then click through the various tablets in the workflow panel to evaluate the various aspects of the lesion. As each tablet is selected, the corresponding layout is displayed with the finding in view (as a result of the current 3D navigation point) regardless of the zoom level and orientation of the image. This is also a key factor in making the unilateral layouts work efficiently, since the current 3D navigation point reflects the left/right side.

Zoom and Pan. It is fairly common for various MR series to be acquired of different fields of view and/or at different spatial resolutions. A field of view refers to the area of the anatomy shown in the image, such as a two centimeter (cm) by two cm field of view. A spatial resolution refers to the spatial distance represented by each pixel, such as a 0.01 cm/Pixel.

For example, since the timing of the series in temporal scans is important, there is a tradeoff in spatial resolution in order to scan as often as desired. Therefore, another high resolution acquisition may be done to be able to better assess the morphology and detailed characteristics of the anatomy. The high resolution scan may be at the same field of view, but have a higher spatial resolution resulting in more image pixels. For example, the temporal series may contain images of 512×512 pixels, but the high resolution series may contain images of 1024×1024 pixels. Similarly, some acquisitions take longer, thus are limited on the resolution, so they may result in a 256×256 image. Also, it may be common to acquire images at a different field of view. For example, in prostate studies, it is common to acquire some series with the full pelvis in the field of view, while other series are acquired focused on just the prostate, so they have a smaller field of view. Yet, the user would like to view all of these different series side by side. While viewing the images, it is desirable for the same feature to appear the same size in all of the various series, otherwise it creates confusion.

From a workflow standpoint, it is common to link images in the same plane so they zoom and pan together. When the images have a different spatial resolution (i.e., the millimeters per pixel differs), or different field of view (i.e., image spatial size varies), it is difficult to get them to zoom using the traditional zoom methods such that the feature of interest is displayed as the same size in all images. Unlinking the images means the user has to individually zoom each series. There is also time wasted by the user panning the images so the area of interest is in the viewable area as images are zoomed. The goal of the user is to display the same field of view in all of the series in the same plane.

Another problem with the traditional zoom methods is demonstrated as you change display stations. Many systems save the zoom level with the hanging protocols. However, the zoom level is based on the ratio of image pixels to display pixels. Thus, 1× zoom is where each pixel of the image data is shown directly as a single pixel on the display. If the configuration of the display differs between display stations, the saved zoom level at one machine will not be the ideal level for another machine. For example, to display the full 512×512 pixel image on a 1024×1024 pixel display would require a 2× zoom level. However, if you load that same image on a 512×512 pixel display, a 1× zoom level would be desired to view the entire image since the 2× zoom level would display only one fourth of the image. Many radiologic display stations handle the simple case of "fit image to window" which would set the appropriate zoom level such that the full image fits in the current window size. However, when saving the layout, there are many times it is useful to save a zoomed image. In those cases, the user is primarily setting up the field of view they would like to be displayed on the screen, and it is not the full image.

To address these issues, the system 100 uses a spatial zoom level and field of view for handling the zoom. The spatial zoom level is millimeters per display pixel, versus the pixel zoom level which is image pixel per display pixel. Thus, images of different spatial resolution, image size, or field of view can all be displayed at the same zoom level resulting in a feature being the same size for all images. FIGS. 9A-9C depict the differences in viewing various images by the traditional pixel zoom and the spatial zoom. FIG. 9A illustrates three images containing the same objects, but with different fields of view or spatial resolution. The traditional pixel zoom method, illustrated in FIG. 9B, holds the ratio of display pixels to image pixels constant, resulting in the objects appearing as different sizes. By contrast, the spatial zoom, shown in FIG. 9C, ensures images in the same plane are showing the features at the same zoom level; that is a 0.5 cm feature is displayed as the same size regardless of the image resolution or field of view (see FIG. 9C). Using a spatial zoom method allows users to link series so they zoom and pan together (rather than adjusting each series individually), regardless of the field of view or spatial resolution of each series.

Additionally, when saving layouts, the spatial field of view shown in each image window is saved. This ensures that the displayed field of view will remain consistent regardless of the display resolution of the display station. Thus, viewing images on different systems will remain consistent relative to the features being viewed.

The spatial zoom is achieved by saving the spatial field of view (FOV) for the zoom level, which is the width and height of the viewed image area in centimeters. To display an image at that zoom level, the pixel zoom level is computed such that the image field of view is fit to the pixel dimensions of the display area. The spatial FOV is adjusted based on the aspect ratio of the display area (width and height in pixels) and the aspect ratio of the zoom level FOV (width and height in centimeters) such that the entire zoom level FOV will still be displayed. For example, if the spatial zoom level FOV is 2×3 cm, but the image display is 200×400 pixels, the spatial FOV is adjusted to 2×4 cm so then entire original FOV is still shown. The computed pixel zoom level is then used to display the image. Below are the calculations:

Spatial zoom level ($FOV_{spatial}$) saved as width and height of the viewed image area in centimeters:

$FOV_{spatial}$.width=viewed image width $FOV_{spatial}$.height=viewed image height To display an image at that zoom level, first compute the adjusted FOV ($FOV_{new}$) based on the window size (display) and zoom level ($FOV_{spatial}$):

```
aspectFOV = FOV_spatial.width / FOV_spatial.height
aspectDisplay = display.width / display.height
if (aspectFOV > aspectDisplay)
    FOV_new.width = FOV_spatial.width
    FOV_new.height = FOV_spatial.height * apsectFOV / aspectDisplay
else
    FOV_new.width = FOV_spatial.width * aspectDisplay / aspectFOV
    FOV_new.height = FOV_spatial.height
```

Finally, the pixel zoom level is computed based on the spatial size of a pixel in the image (imagePixel), the adjusted FOV ($FOV_{new}$), and the window size in pixels (display): (assumes pixels in the image and display are square)

pixelZoom=imagePixel·width/$FOV_{new}$·width/ display·width

Using a spatial zoom also allows the layout zoom levels to be relative to the size of the lesion. For example, the layout used to assess morphology is most useful when the images are automatically zoomed. The layout could be saved so it would automatically zoom to fit the size of the lesion to the view area, providing an adaptable zoom specific to the lesion of interest. This significantly adds to the efficiency of interrogating suspicious areas in the medical image data.

Parametric Maps. Parametric maps are computed to show an aspect of the series based on some set of parameters. The resulting maps are typically colorized overlays that may be displayed on top the source image(s) to allow the user to correlate some parameters to specific areas of the image. An example is a kinetic map which may show the uptake and/or washout characteristics based on a set of dynamic series (a temporal data set of series taken at timed intervals). It is often desirable to show these overlays on other images—those that were not used to compute the parametric map. For example, in order to correlate the kinetic map with other non-temporal series that are also used for diagnosis, it is desirable to show the overlay on these other images. In addition, the user would like to view the kinetic curve (a plot if the intensities over time from the temporal series), which are the basis for the kinetic map, at any location of any series. The overlay can be reformatted to match the field of view and orientation of any other series in the study, thus allowing the overlay to be displayed on other series. In addition, the spatial position of any area of interest on any series in the study can be used to then plot the kinetic curve based on the same spatial position in the temporal series. Refer to FIGS. 10A-10B for an example study showing a kinetic map overlaid on the original series. FIG. 10A illustrates reformats of the kinetic series, on a high resolution series, and on a STIR series. The high resolution and STIR series are different spatial resolutions and fields of view than the original temporal series. FIG. 10B shows an example of various kinetic curve plots that were generated based on the special location of the various series (reformats, high resolution acquisition, or STIR) then transposed to the position in the temporal series that is then used to compute the curve to plot.

Sample Workflow Overview. Below is a description of a typical workflow, incorporating the various aspects of the system 100. FIG. 11 shows the specific workflow for reading diagnostic breast MR studies, including some of the tasks associated with each step. This is just one example study type, but those skilled in the art will appreciate how it could easily be applied to other study types as well. This workflow example assumes the user has already saved their desired hanging protocols, including assigning layouts to each of the tablets where appropriate. The hanging protocols are associated with a study protocol (such as sagittal breast studies), so the layouts are then available for all similar studies.

Open Study for review. As users create hanging protocols, they can specify the order of them in the list. When the user opens a study for review, the system starts with the first hanging protocol. It is also easy to switch to the next and previous hanging protocol by clicking on the corresponding buttons in the user interface, or using defined quick keys. This is standard practice in most radiological viewing stations.

Identify overall findings. Users typically have a standard layout used to evaluate the overall findings. In the breast application, a hanging protocol may be assigned to the Summary tablet, which is also where the user identifies the overall assessment (see FIG. 12). In this example, the layout contains a maximum intensity projection (MIP) image (top image) and a T1-weighted image (bottom image), which together can be used to assess the background parenchymal enhancement density and symmetry. Based on the features of the system 100, a single click on the summary tablet selects the hanging protocol and opens the tablet to allow the user to record the overall findings. Users can then navigate through the images, zoom, pan, and turn the parametric maps on or off as desired.

Identify lesions of interest. Users can assign a hanging protocol used for reviewing the study and identifying potential areas of interest to the Findings tablet. As users scroll through the images, they can click on a potential finding and it is added to the list of findings. See FIG. 13 for an example hanging protocol used for review, and a view of the findings list. The Findings list in the example of FIG. 13 shows 2 regions of interest that have been identified.

Perform evaluation, measurements, and assessment of lesions. Once a finding is in the list, the user can interrogate it for further evaluation by selecting it from the list or clicking on it in the image. As a finding is selected, all image areas are synchronized to the centroid 3D location of the finding (or the click point if it was selected from the image). The user can then quickly step through the various tablets to evaluate the finding: Location and Size, Morphology, Kinetics, and Assessment. At each tablet, the appropriate tasks are displayed, any chosen hanging protocol will be applied, and the tools and/or data needed for each task are automatically displayed.

The Location and Size tablet is typically assigned a hanging protocol showing multi-planar reformats to better assess the size and location relative to landmarks. The tablet displays the location, distances to landmarks, and size, along with the tools to adjust these measurements. When the Location and Size tablet is selected, the 3D navigation point is set to the centroid of the lesion, so all of the images are updated to that location. The longest diameters are annotated on the image at that location as well. After a single click to select the tablet, the user is ready to assess the size and location, and make any adjustments necessary. FIG. 14 is an example of the Location and Size tablet and associated hanging protocol. Note that the location/measurement tools are automatically displayed when this panel opens.

The Morphology tablet is typically assigned a hanging protocol showing zoomed images of various acquisitions to be able to assess the shape, margins, distribution, and enhancement characteristics. The images may be automatically zoomed to a level that fits the entire lesion within the window based on the lesion size. In the breast application, the Morphology tablet displays the ACR BI-RADS recommended morphology classifications. The user can quickly and easily click on the appropriate classifications based on the image views. FIG. 15 is an example of the Morphology tablet and associated hanging protocol.

The Kinetics tablet is typically assigned a hanging protocol showing the temporal series, subtractions, and parametric maps that depict the kinetic behavior. With the ability to overlay the parametric map on any series, regardless of its orientation or field of view, the user can correlate the parametric map with features on the non-temporal series. The ACR BI-RADS recommends the user report the kinetic curve peak and curve type for the most-enhancing area of the lesion. In the breast application, the system 100 automatically computes the kinetic curve with the highest uptake within the lesion. This process is described in U.S. Pat. No. 72,251,374, entitled SYSTEM AND METHOD FOR HIERARCHICAL ANALYSIS OF CONTRAST ENHANCED MEDICAL IMAGING INFORMATION, which is assigned to the assignee of the present application.

When the user selects the Kinetics tablet, the 3D navigation point is set to the location of the computed curve, and that location is annotated on the images. The curve is shown in the tablet, along with the kinetic composition of the lesion. FIG. 16 is an example of the Kinetics tablet and associated hanging protocol.

The Assessment tablet is where the user will enter the final assessment for that lesion (such as the BI-RADS assessment in breast, or the staging results in other applications), the recommendation (biopsy, follow-up, etc.), and comments. A MIP is typically shown with the Assessment tablet since it shows a nice overview of the breast. FIG. 17 is an example of the Assessment tablet and associated hanging protocol.

With the features in the system 100, the user can quickly click on the various tablets that represent the key attributes to assess the lesions. With a single click on each tablet, the hanging protocol changes to show the lesion location in the desired images at the appropriate zoom level. That is quite a contrast from typical radiological viewing systems, where the user would click to change the hanging protocol, then scroll and navigate to the lesion location, then zoom and pan as desired, and somehow interact with the system to perform the measurements and record the information—and that would be the process for each step of evaluation (location and size, morphology, kinetics, and assessment).

Report lesions. Users can assign a layout to the Auto Portfolio-Findings tablet. This tablet provides some additional efficiency by automating the reporting of the findings. The breast application provides an automatic report (the Auto Portfolio), which includes all of the findings data from the previous tablets, plus automatic snapshots of the key images for each finding in the list. The user chooses the desired series for the snapshots, including the zoom level and whether parametric maps are shown by simply setting up the hanging protocol for this tablet. The automated snapshots of the key images in the layout are captured at the centroid location of the lesion. Similarly, when the user clicks on the Auto Portfolio-Findings tablet, the 3D navigation point is set to the centroid of the lesion. This allows the user to see the key images that are automatically captured. If the user desires to change any of the images for a particular lesion, they simply change the image, series, parametric map overlay, and zoom level to show the desired views. Then the user clicks on a button to override the automatic snapshots with those pictures. FIG. 18 is an example of the Auto Portfolio—Findings tablet and associated hanging protocol. Obviously, the automatic reporting of the data and key images has a huge impact on efficiency. However, the system 100 also makes setting up the automatic reporting very efficient by using the hanging protocol assigned to the tablet. That coupled with the easy method for overriding the key images with a single click makes it flexible and efficient.

In addition to the automatic snapshot of key images, the automatic report also includes all of the findings data from the previous tablets (location and size, morphology, kinetics, and assessment). The user also has the option to easily dictate the results by just reviewing the data shown in the lesion panel. With the Auto Portfolio-Findings tablet selected, all other tablets are in their collapsed view, thus showing the results of each evaluation while also viewing the key images chosen to represent that finding. The tablets are listed in dictation order, making it very efficient to describe each lesion. From this view, the user can simply click each lesion in the findings list and see the key images and associated data for each one.

Report overall findings. In the summary panel, the Auto Portfolio—Summary tablet allows users to choose some series that show all of the lesions of interest. In breast, these are typically MIP images with the lesions highlighted. Similar to the key images for each finding, the automatic report can also be configured to include automatic snapshots of these summary images. The entire summary panel also provides a nice overview of the overall findings and summary of the lesions for easy dictation. FIG. 19 is an example of the Auto Portfolio—Summary tablet and associated hanging protocol.

This breast example shows how the workflow panel with tablets for each task provides efficiency for the user. By assigning the tools and hanging protocols to each tablet, the user can quickly step through the tasks in a workflow. The 3D navigation point and spatial zoom are essential to streamlining the workflow by significantly reducing the actions required by the user as they transition between tasks and perform each step. Handling the unilateral series in the hanging protocols, integrated with the 3D navigation significantly simplifies reviews of left/right split studies. Having the ability to overlay the parametric map on any series, regardless of its orientation or field of view, also significantly improves the ability to correlate the parametric map with features on the non-temporal series. The workflow efficiency includes both productivity of reading a study, but also efficiency gained by essentially training the staff on the aspects of reading cases because the workflow panel and tablets basically provide a checklist of the features to review and evaluate. In addition, by allowing a site to associate hanging protocols to the tasks, this ensures the staff is reviewing the desired images while making the evaluations.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A system for viewing medical images and associated medical data, comprising:
   a data storage structure configured to store a plurality of workflow processes;
   an interface to receive the medical images and associated medical data;
   a display device to display at least a portion of the medical image data;
   a user-operable input device; and
   a processor configured to accept user input from the input device to select a workflow process from among a plurality of workflow processes, the selected workflow process comprising a plurality of workflow panels displayed on the display device wherein each of the plurality of a workflow panel displays tablets for tasks in the workflow, with the appropriate data and tools in the tablet panel.

2. The system of claim 1 wherein the display device displays the tablet panel with an expanded view unveiling all of the data and tools, or with a collapsed view displaying the key data to report for that task.

3. The system of claim 1 wherein there is an assigned hanging protocol for viewing a series of medical images associated with the data and tools in the tablet panel, and selecting the tablet panel causes the display device to display data in the tablet panel and image panels in accordance with the assigned hanging protocol.

4. The system of claim 3 wherein after the display device displays medical images in the tablet panel in accordance with the assigned hanging protocol, the processor is further configured to automatically pan the medical images so a current three dimensional (3D) spatial focus point is in view on the display device.

5. The system of claim 3 wherein after the display device displays medical images in the tablet panel in accordance with the assigned hanging protocol, the processor is further configured to automatically set a three dimensional (3D) spatial focus point based on a selected region of interest in the displayed medical image in the tablet, and the displayed medical image is automatically panned so the new 3D spatial focus point is in view on the display device.

6. The system of claim 1 wherein the processor is further comprising a spatial zoom level for the medical images displayed on the display device.

7. The system of claim 6 where the hanging protocol includes a spatial zoom level relative to a selected region of interest in the displayed medical image.

8. A system for viewing medical images and associated medical data, comprising:
   a data storage structure configured to store a plurality of workflow processes;
   an interface to receive the medical images and associated medical data;
   a display device to display at least a portion of the medical image data:
   a user-operable input device; and
   a processor configured to accept user input from the input device to select a portion of the medical images comprising a left-side unilateral series and a corresponding right-side unilateral series, the processor having a single hanging protocol associated with the selected portion of the medical images wherein the processor switches the single hanging protocol assigned to one of the left side and right side unilateral series wherein the processor applies the single hanging protocol to the other of the left side and right side unilateral series.

9. The system of claim 8 wherein a button operable by a user can be used to switch between the left side and right side unilateral series.

10. The system of claim 8 wherein the display device automatically switches between the left side and right side unilateral series based on a current spatial point of focus on the display device.

11. The system of claim 8 wherein the display device automatically switches between the left side and right side unilateral series based on a user selection of lesion whose location is used to determine which of the left side and right side unilateral series to display.

12. A system for viewing medical images and associated medical data, comprising:
    a data storage structure configured to store a plurality of workflow processes;
    an interface to receive the medical images and associated medical data;
    a display device to display at least a portion of the medical image data;
    a user-operable input device; and
    a processor configured to accept user input from the input device to select a portion of the medical images for display, the processor being further configured to generate a current three dimensional (3D) spatial focus location on a medical image displayed on the display device wherein the processor determines the current 3D focus location in the others of the medical images as the others of the medical images are newly displayed on the display device to thereby automatically update the medical images to view the current 3D spatial focus location as the newly displayed images are displayed on the display device.

13. The system of claim 12 wherein the processor automatically determines the current 3D spatial focus point in a different series of medical images to thereby automatically select one of the medical images in the new series that corresponds to the current 3D spatial focus point.

14. The system of claim 12 wherein the processor applies a hanging protocol to the medical image on the display device and automatically determines the current 3D spatial focus point in medical image to thereby automatically position the current 3D spatial focus point in the medical image in response to changes in the hanging protocol.

15. The system of claim 12 wherein the processor is configured to set the current 3D focus location in response to user operation of the input device to click on a location in the medical image displayed on the display device.

16. The system of claim 12 wherein the processor is configured to set the current 3D focus location in response to user operation of the input device to click on a lesion, finding, or other object in the displayed medical image.

17. The system of claim 12 wherein the processor is configured to set the current 3D focus location in response to user operation of the input device to click on a displayed list.

18. The system of claim 12 wherein the processor is configured to display different ones of medical images in a display in response to user operation of the input device to scroll through the medical images in the series in a user-selected direction wherein the processor is configured to update the current 3D focus location only in a vector direction in which the user is scrolling through the medical images in the series.

19. The system of claim 12 wherein the processor is configured to set the current 3D focus location in response to user operation of the input device to zoom in the displayed medical image wherein the center of the zoomed image is used to set the current 3D focus location.

20. The system of claim 12 wherein the processor is configured to automatically pan the displayed medical image so the 3D focus location is within view on the display device in response to the application of a hanging protocol to the displayed medical image that results in a zoomed medical image.

21. The system of claim 12 wherein the processor is configured to automatically pan the displayed medical image so the 3D focus location is within view on the display device in response to the selection of a different series of medical images that results in a zoomed medical image.

22. A system for viewing medical images and associated medical data comprising:
- a data storage structure configured to store a plurality of workflow processes;
- an interface to receive the medical images and associated medical data;
- a display device to display at least a portion of the medical image data;
- a user-operable input device; and
- a processor configured to accept user input from the input device to select a portion of the medical images for display, the processor being further configured to generate a zoom image for display wherein medical images in the same plane are linked and zoom to the same spatial zoom level, wherein a feature in the medical images is displayed as the same size in all image views regardless of the original spatial resolution, size, or field of view of each of the images.

23. The system of claim 22 wherein a spatial field of view is saved in a hanging protocol to thereby provide consistent views regardless of the display resolution of various display stations using the hanging protocol.

24. The system of claim 22 wherein a spatial field of view is relative to a selected image feature.

25. A system for viewing medical images and associated medical data comprising:
- a data storage structure configured to store a plurality of workflow processes;
- an interface to receive the medical images and associated medical data;
- a display device to display at least a portion of the medical image data:
- a user-operable input device; and
- a processor configured to accept user input from the input device to select a portion of the medical images for display, the processor being further configured to generate display data wherein a parametric map overlay is reformatted to match a field of view and orientation of any other series in the study so the computed parametric maps can be overlaid on those series.

26. A method for viewing medical images and associated medical data, comprising:
- storing a plurality of workflow processes;
- receiving the medical images and associated medical data;
- displaying at least a portion of the medical image data on a display device;
- a user-operable input device; and
- in response to user input from the input device to select a workflow process from among a plurality of workflow processes, displaying the selected workflow process comprising a plurality of workflow panels displayed on the display device wherein each of the plurality of a workflow panel displays tablets for tasks in the workflow, with the appropriate data and tools in the tablet panel.

* * * * *